United States Patent
Hong et al.

(10) Patent No.: US 11,000,537 B2
(45) Date of Patent: May 11, 2021

(54) COMPOSITION COMPRISING NOVEL GINSENOSIDE

(71) Applicant: AMOREPACIFIC CORPORATION, Seoul (KR)

(72) Inventors: Yong Deog Hong, Yongin-si (KR); Hyun Woo Jeong, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 0 days.

(21) Appl. No.: 16/656,029

(22) Filed: Oct. 17, 2019

(65) Prior Publication Data
US 2020/0123194 A1    Apr. 23, 2020

(30) Foreign Application Priority Data

| Oct. 17, 2018 | (KR) | 10-2018-0123960 |
| Oct. 17, 2018 | (KR) | 10-2018-0123965 |
| Oct. 31, 2018 | (KR) | 10-2018-0132429 |
| Nov. 1, 2018  | (KR) | 10-2018-0132850 |
| Sep. 26, 2019 | (KR) | 10-2019-0119056 |

(51) Int. Cl.
*A61K 31/7048* (2006.01)
*A61P 3/10* (2006.01)
*C07J 17/00* (2006.01)

(52) U.S. Cl.
CPC ........... *A61K 31/7048* (2013.01); *A61P 3/10* (2018.01); *C07J 17/005* (2013.01)

(58) Field of Classification Search
None
See application file for complete search history.

(56) References Cited

U.S. PATENT DOCUMENTS 8,440,632 B2 * 5/2013 Daley .................. A61P 9/02
                                                 514/26

FOREIGN PATENT DOCUMENTS

| CN | 102875628 A    | 1/2013  |
| CN | 102924556 A    | 2/2013  |
| KR | 10-0178867 B1  | 3/1999  |
| KR | 10-1312389 B1  | 9/2013  |
| KR | 10-1568658 B1  | 11/2015 |
| KR | 10-2016-0086149 A | 7/2016 |
| WO | 2005/000245 A2 | 1/2005  |
| WO | 2005/000248 A1 | 1/2005  |
| WO | 2005/040189 A1 | 5/2005  |

OTHER PUBLICATIONS

Rho, T., Jeong, H. W., Hong, Y. D., Yoon, K., Cho, J. Y., & Yoon, K. D. (2020). Identification of a novel triterpene saponin from Panax ginseng seeds, pseudoginsenoside RT8, and its antiinflammatory activity. Journal of ginseng research, 44(1), 145-153. (Year: 2020).*

Kim, J. H. (2018). Pharmacological and medical applications of Panax ginseng and ginsenosides: a review for use in cardiovascular diseases. Journal of ginseng research, 42(3), 264-269. (Year: 2018).*

Prabhakar, P. K., & Doble, M. (2011). Mechanism of action of natural products used in the treatment of diabetes mellitus. Chinese Journal of Integrative Medicine, 17(8), 563. (Year: 2011).*

Kim, J. K., Kim, B. S., Park, C. W., Seo, D. B., Yoo, H. R., & Lee, S. J. (2010). Effect of ginseng-berry extract on the improvement of blood microcirculation and skin brightness. Journal of Physiology & Pathology in Korean Medicine, 24(1), 85-90. (Year: 2010).*

Yang Jie, et al., "Semisynthesis and Cytotoxicity Evaluation of a Series of Ocotillol Type Saponins and Aglycones from 20(S)-Ginsenoside Rg2, Rh1, Protopanaxatriol and Their 20(R)-Epimers", Chem. Res. Chin. Univ., 2016, vol. 32, No. 1, pp. 35-40.

CAS RN : 2170771-84-1.

* cited by examiner

*Primary Examiner* — Dale R Miller
(74) *Attorney, Agent, or Firm* — Merchant & Gould P.C.

(57) ABSTRACT

The present specification relates to a composition containing novel ginsenoside, (20S,24R)-6-O-β-D-glucopyranosyl (1→2)-β-D-glucopyranoside-dammar-3-one-20,24-epoxy-6a,12b,25-triol, a pharmaceutically acceptable salt thereof, a hydrate or a solvate thereof as an active ingredient. The composition exhibits excellent effects in glycemic control, lipid metabolic control, cholesterol control, anti-obesity and blood circulation improvement.

17 Claims, 36 Drawing Sheets

Chemical Formula: $C_{42}H_{72}O_{14}$
Exact Mass: 800.4922

1. Ginsenoside Rg1

Chemical Formula: $C_{42}H_{72}O_{13}$
Exact Mass: 784.4973

2. (20S)-Ginsenoside Rg2

Chemical Formula: $C_{48}H_{82}O_{18}$
Exact Mass: 946.5501

3. Ginsenoside Re

Chemical Formula: $C_{48}H_{82}O_{18}$
Exact Mass: 946.5501

4. Ginsenoside Rd

Chemical Formula: $C_{54}H_{92}O_{23}$
Exact Mass: 1108.6029

5. Ginsenoside Rb1

Chemical Formula: $C_{53}H_{90}O_{22}$
Exact Mass: 1078.5924

6. Ginsenoside Rb2

SREBP1c

COMPOSITION COMPRISING NOVEL GINSENOSIDE

CROSS-REFERENCE TO RELATED APPLICATION

This application claims priority to Korean Patent Application No. 10-2018-0123960 filed on Oct. 17, 2018, Korean Patent Application No. 10-2018-0123965 filed on Oct. 17, 2018, Korean Patent Application No. 10-2018-0132429 filed on Oct. 31, 2018, Korean Patent Application No. 10-2018-0132850 filed on Nov. 1, 2018 and Korean Patent Application No. 10-2019-0119056 filed on Sep. 26, 2019, and all the benefits accruing therefrom under 35 U.S.C. .sctn.119, the contents of which in its entirety are herein incorporated by reference.

BACKGROUND OF THE INVENTION

Field of the Invention

The present specification describes novel ginsenosides and compositions comprising the same.

Description of the Related Art

Ginseng (*Panax Ginseng* C. A. Meyer) is a plant belonging to the genus *Panax* of the family Araliaceae. It has been used as herbal medicine from 2,000 years ago in Korea, China, Japan, etc. As the representative physiologically active ingredients of *Ginseng*, saponins, polysaccharides, peptides, sitosterols, polyacetylenes and fatty acids are known, and among them, saponins of *Ginseng* are called ginsenosides. The effects and efficacies of *Ginseng* comprise action on the central nervous system, anticarcinogenic action, anticancer activity, immunomodulatory action, antidiabetic action, liver function improving effect, action of improving cardiovascular disorders, anti-atherosclerotic action, blood pressure controlling action, action of improving menopausal disorder, effect on osteoporosis, anti-stress action, anti-fatigue action, antioxidant action, antiaging effect, etc. The ginsenoside has a large difference in its content and composition depending on the parts such as roots, leaves, fruits, flowers, seeds, etc. of *Ginseng*, but the efficacy known as above is mostly about the *Ginseng* root, namely, the root part of *Ginseng*, and research on other parts of *Ginseng* except *Ginseng* root is insufficient

CITATION LIST

Patent Literature

Patent Literature 1: Korean Patent Application Publication No. 10-2016-0086149

SUMMARY OF THE INVENTION

In one aspect, the technical problem of the present invention is to provide a composition comprising a novel ginsenoside having excellent metabolic control efficacy.

In one aspect, the technical problem of the present invention is to provide a composition comprising a novel ginsenoside having excellent glycemic control efficacy.

In one aspect, the technical problem of the present invention is to provide a composition comprising a novel ginsenoside having excellent lipid metabolic controlling capacity.

In one aspect, the technical problem of the present invention is to provide a novel ginsenoside having excellent cholesterol controlling capacity.

In one aspect, the technical problem of the present invention is to provide a composition comprising a novel ginsenoside having excellent anti-obesity efficacy.

In one aspect, the technical problem of the present invention is to provide a composition comprising a novel ginsenoside having excellent blood circulation improving efficacy.

In one aspect, the present disclosure provides a composition for controlling metabolism comprising (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient.

In one aspect, the present disclosure provides a composition for controlling blood sugar comprising (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient.

In one aspect, the present disclosure provides a composition for controlling or inhibiting lipid metabolism comprising (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient.

In one aspect, the present disclosure provides a composition for controlling cholesterol comprising (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient.

In one aspect, the present disclosure provides an anti-obesity composition comprising (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient.

In one aspect, the present disclosure provides a composition for improving blood circulation comprising (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient.

In one aspect, the present disclosure may provide a composition comprising a novel ginsenoside, a pharmaceutically acceptable salt thereof, a hydrate or solvate thereof having an excellent effect on blood sugar control. The novel ginsenosides exhibit excellent blood sugar control, lipid metabolic control or inhibition, cholesterol control, anti-obesity and blood circulation improving efficacy.

DETAILED DESCRIPTION OF THE PREFERRED EMBODIMENTS

Figure 1:
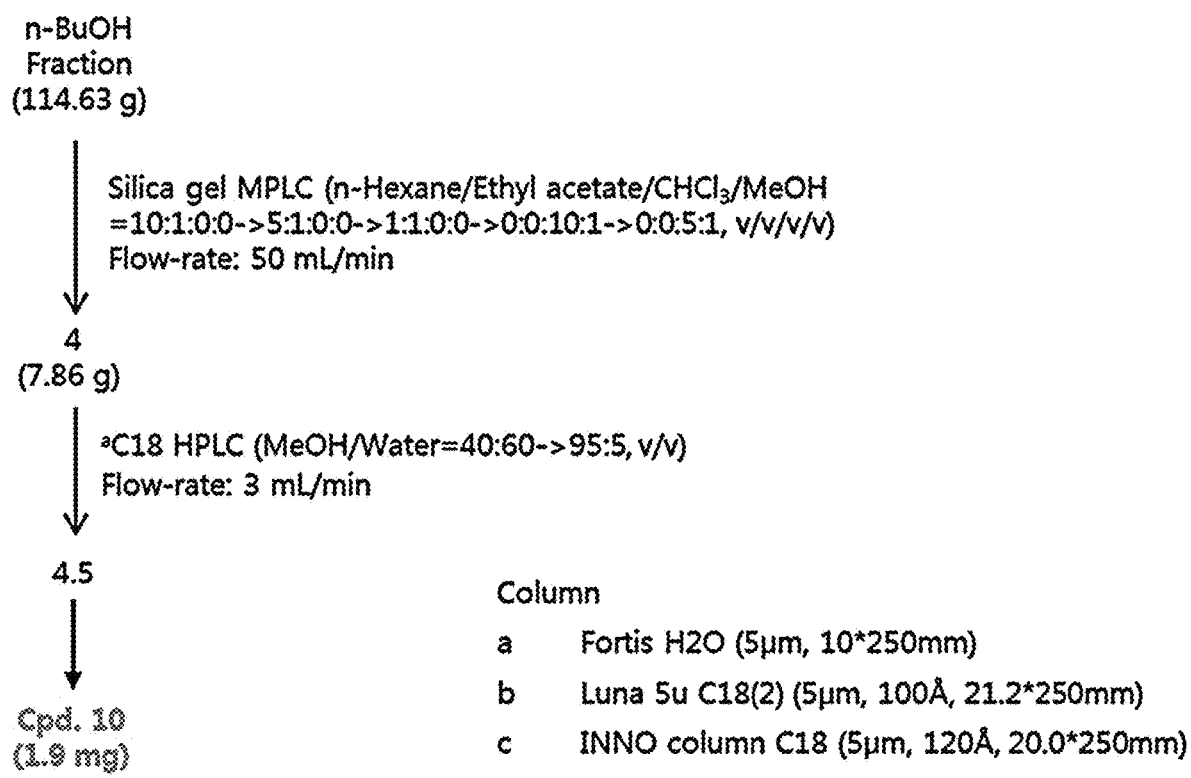
FIG. 1 is a diagram illustrating an isolation process of a novel ginsenoside (Cpd. 10) of the present disclosure among the compounds fractionated from *Ginseng* seed extract.

Hereinafter, embodiments of the present disclosure will be described in more detail with reference to the accompanying drawings. However, the technology described in the present disclosure is not limited to the embodiments described herein and may be embodied in other forms. It is to be understood that the embodiments introduced herein are provided so that the disclosure can be made thorough and complete, and that the spirit of the present disclosure can be fully conveyed to those skilled in the art. In order to clearly express each constituent in the drawings, the size, such as the width or thickness, etc. of the constituent, is shown to be somewhat enlarged. In addition, although only a part of the constituents are shown for convenience of explanation, those skilled in the art will be able to easily understand the rest parts of the constituents. In addition, those having ordinary skill in the pertinent field may implement the spirit of the present disclosure in various other forms without departing from the technical spirit of the present disclosure.

In one embodiment, the present disclosure may provide a composition for controlling metabolism comprising a novel ginsenoside, a pharmaceutically acceptable salt thereof, a hydrate or a solvate thereof as an active ingredient.

In one embodiment, the present disclosure may provide a composition for controlling blood sugar comprising a novel ginsenoside, a pharmaceutically acceptable salt thereof, a hydrate or a solvate thereof as an active ingredient.

In one embodiment, the present disclosure may provide a composition for controlling or inhibiting lipid metabolism comprising a novel ginsenoside, a pharmaceutically acceptable salt thereof, a hydrate or a solvate thereof as an active ingredient.

In one embodiment, the present disclosure may provide a composition for controlling cholesterol comprising a novel ginsenoside, a pharmaceutically acceptable salt thereof, a hydrate or a solvate thereof as an active ingredient.

In one embodiment, the present disclosure may provide an anti-obesity composition comprising a novel ginsenoside, a pharmaceutically acceptable salt thereof, a hydrate or a solvate thereof as an active ingredient.

In one embodiment, the present disclosure may provide a composition for improving blood circulation comprising a novel ginsenoside, a pharmaceutically acceptable salt thereof, a hydrate or a solvate thereof as an active ingredient.

In one embodiment, the ginsenoside is a novel triterpene saponin, and is (20S,24R)-6-O-β-D-glucopyranosyl(1→2)-β-D-glucopyranoside-dammar-3-one-20,24-epoxy-6a,12b,25-triol.

One embodiment may provide a use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof for use in the preparation of a composition for controlling metabolism.

One embodiment may provide a method of controlling metabolism comprising administering (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof in an effective amount to a subject in need thereof. In one embodiment, the method may comprise administering to a subject with reduced metabolic control capacity.

One embodiment may provide (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for use in a composition for controlling or inhibiting metabolism. In addition, a non-therapeutic use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof may be provided as an active ingredient for metabolic control or inhibition.

In one embodiment, there may be provided a use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof for use in the preparation of a composition for blood sugar control.

In one embodiment, there may be provided a method for controlling blood sugar comprising administering to a subject in need thereof an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof. In one embodiment, the method may comprise administering to a subject with reduced blood sugar control capacity.

In one embodiment, there may be provided (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient for use in a composition for controlling blood sugar. In addition, there may be provided a non-therapeutic use of (20S,24R)-6-O-β-D-glucopyranosyl (1→2)-β-D-glucopyranoside-dammar-3-one-20,24-epoxy-6a,12b,25-triol, a pharmaceutically acceptable salt thereof, a hydrate or a solvate thereof as an active ingredient for controlling blood sugar.

One embodiment may provide a use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof for use in the preparation of a composition for controlling or inhibiting lipid metabolism.

One embodiment may provide a method of controlling or inhibiting lipid metabolism comprising administering (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof in an effective amount to a subject in need thereof. In one embodiment, the method may comprise administering to a subject with reduced lipid metabolic control capacity.

One embodiment may provide (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for use in a composition for controlling or inhibiting lipid metabolism. In addition, a non-therapeutic use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for lipid metabolic control or inhibition may be provided.

One embodiment may provide a use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof for use in the preparation of a composition for controlling cholesterol.

One embodiment may provide a method of controlling cholesterol comprising administering (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof in an effective amount to a subject in need thereof. In one embodiment, the method may comprise administering to a subject with reduced cholesterol metabolic control capacity.

One embodiment may provide (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for use in a composition for controlling cholesterol. In addition, a non-therapeutic use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for cholesterol control may be provided One embodiment may provide a use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof for use in the preparation of an anti-obesity composition.

One embodiment may provide an anti-obesity method comprising administering (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof in an effective amount to a subject in need thereof. In one embodiment, the method may comprise administering to an obese subject.

One embodiment may provide (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for use in an anti-obesity composition. In addition, a non-therapeutic use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for anti-obesity may be provided.

One embodiment may provide a use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof for use in the preparation of a composition for improving blood circulation.

One embodiment may provide a method of improving blood circulation comprising administering (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof in an effective amount to a subject in need thereof. In one embodiment, the method may comprise administering to a subject with poor blood circulation.

One embodiment may provide (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for use in a composition for improving blood circulation. In addition, a non-therapeutic use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for blood circulation improvement may be provided.

As used herein, the term "pharmaceutically acceptable" refers to those that can be approved or was approved by the government or equivalent regulatory agencies for use in animals, more specifically in humans, by avoiding significant toxic effects when used in conventional medicinal dosage, or those recognized as being listed in the pharmacopoeia or described in other general pharmacopoeia.

As used herein, the term "pharmaceutically acceptable salt" refers to a salt according to one aspect of the present disclosure that is pharmaceutically acceptable and possesses the desired pharmacological activity of the parent compound. The salts comprise (1) acid addition salts, formed with inorganic acids such as hydrochloric acid, hydrobromic acid, sulfuric acid, nitric acid, phosphoric acid, or the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, or the like; or (2) salts formed when an acidic proton present in the parent compound is substituted.

As used herein, the term "hydrate" refers to a compound to which water is bound, and is a broad concept comprising an inclusion compound having no chemical bonding force between water and the compound.

As used herein, the term "solvate" refers to a compound of higher order produced between molecules or ions of a solute and molecules or ions of a solvent.

In one embodiment, the molecular formula of ginsenoside is $C_{42}H_{70}O_{15}$, and has the following chemical structure.

[Formula 1]

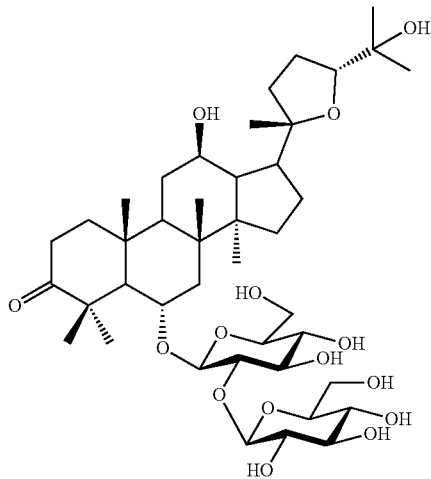

In the present specification, the novel ginsenosides are named "pseudoginsenoside $RT_8$" or "PG-$RT_8$."

In one embodiment, the ginsenoside may be isolated from the Ginseng seed extract, but is not limited thereto. In one embodiment, the Ginseng of the Ginseng seed is Panax Ginseng C. A. Meyer.

As used herein, the term "isolation" is meant to comprise those extracted or fractionated from Ginseng seed extract, and may use water, organic solvents, or the like, and any method known to those skilled in the art may also be applied. The fraction may be performed after the extraction.

As used herein, the term "extract" means a substance obtained by extracting a component contained inside of a natural substance, regardless of the extracted method or ingredients. The term is used in a broad sense comprising, for example, all of those obtained by extracting a component soluble in a solvent from a natural substance using water or an organic solvent, extracting only a specific component of a natural substance, or the like.

As used herein, "fractions" comprise those obtained by fractionating a specific substance or extract using a certain solvent or those leftover after fractions, and extracting them again with a specific solvent. Fractional methods and extraction methods may be any method known to those skilled in the art.

As used herein, the term "prevention" refers to any action that inhibits or delays a desired symptom by administering a composition according to one embodiment of the present disclosure. As used herein, the term "treatment" refers to any action that improves or disappears a desired symptom or disease by administering a composition according to one embodiment of the present disclosure. As used herein, the term "improvement" refers to any action in which a desired symptom is improved or advantageously changed from before administration by administering a composition according to one embodiment of the present disclosure.

In one embodiment, the ginsenoside may be isolated from Ginseng seed methanol- and butanol-soluble extract.

Specifically, the ginsenoside may be detected and isolated by analyzing methanol- and butanol-soluble extracts of Ginseng seed using HPLC-ESI-Q-TOF-MS. Not all triterpenes and steroidal saponins can be observed by HPLC-UV or HPLC-ELSD from Ginseng seed crude extract because the main component of Ginseng seed extract is lipid.

In one embodiment, the present disclosure may provide a composition for lowering blood sugar by comprising the ginsenoside, a pharmaceutically acceptable salt thereof, a hydrate thereof, or a solvate thereof. In one embodiment, the active ingredient may inhibit glycolysis in the blood or promote cellular uptake of glucose in the blood. Thus, in one embodiment, the composition according to the present disclosure may prevent or treat diabetes or diabetes complications or glucometabolic disorder. "Diabetes" refers to a disease in which glucoses are discharged in urine as blood sugar is not controlled since sugar in the blood cannot be used when a balance between in vivo insulin sensitivity and insulin secretion is broken, that is, when the insulin is deficient or the insulin sensitivity is reduced. The diabetic complications may be divided into acute complications and chronic complications. Examples of the acute complications comprise ketoacidosis, hyperosmotic hyperglycemia syndrome, hypoglycemia, or the like. Examples of the chronic complications comprise, but are not limited to, large vessel complications such as coronary artery disease, cerebrovascular disease, peripheral vascular disease, or the like, microvascular complications such as diabetic retinopathy, diabetic nephropathy, diabetic neuropathy, or the like, and diabetic foot lesions, or the like.

In one embodiment, the present disclosure may provide a composition having remarkably excellent blood sugar control efficacy as compared to conventional ginsenosides known to have blood sugar control efficacy.

In one embodiment, the present disclosure may comprise the ginsenoside, a pharmaceutically acceptable salt thereof, a hydrate thereof, or a solvate thereof, thereby providing a composition for controlling or inhibiting lipid metabolism by inhibiting the expression of a lipid synthesis gene. In one embodiment, the present disclosure may comprise the ginsenoside, a pharmaceutically acceptable salt thereof, a hydrate thereof, or a solvate thereof, thereby providing a composition for controlling cholesterol metabolism by inhibiting the expression of cholesterol synthesis genes or increasing the expression of genes that lower blood cholesterol levels. The lipid synthesis-related genes comprise, but are not limited to, SREBP1c (sterol-regulatory element binding protein 1c), ACC (acetyl-CoA carboxylase) and FAS (fatty acid synthase). The present disclosure may inhibit the synthesis or accumulation of lipids in the body by inhibiting the expression of the lipid synthesis-related genes as described above, specifically, it may inhibit the accumulation of fat in hepatocytes, or the like. In this case, the lipid may be, for example, triglyceride. In addition, the gene may comprise, but are not limited to, HMG-CoA (3-hydroxy-3-methyl-glutaryl-coenzyme A reductase), LDL receptor (low-density lipoprotein receptor) and SREBP1a (sterol-regulatory element binding protein 1a). The present disclosure may effectively reduce blood cholesterol levels by inhibiting or promoting the expression of the cholesterol synthesis-related genes as described above. In one embodiment, the present disclosure may comprise the ginsenoside, a pharmaceutically acceptable salt thereof, a hydrate thereof, or a solvate thereof, thereby providing a composition for inhibiting lipase activity. The lipase may be, for example, pancreatic lipase. The present disclosure may reduce the lipid concentration in the blood by inhibiting lipolysis in the small intestine by inhibiting the activity of pancreatic lipase. In one embodiment, the present disclosure may comprise the ginsenoside, a pharmaceutically acceptable salt thereof, a hydrate thereof, or a solvate thereof, thereby providing a composition that inhibits lipid degradation in the body.

In one embodiment, the present disclosure may comprise the ginsenoside, a pharmaceutically acceptable salt thereof, a hydrate thereof, or a solvate thereof, thereby providing a composition for preventing or improving metabolic syndrome or dyslipidemia. As used herein, the term "dyslipidemia" refers to a state in which total cholesterol, LDL cholesterol, and triglycerides in blood are increased or HDL cholesterol is decreased than normal, and comprises both genetic and exogenous factors such as diet or drinking. For example, the dyslipidemia may comprise one or more selected from the group consisting of hypertension, diabetes, hyperlipidemia, hypertriglyceridemia, myocardial infarction, angina pectoris, arteriosclerosis, and hypercholesterolemia.

In one embodiment, the present disclosure may provide a composition having a remarkably excellent efficacy for controlling or inhibiting lipid metabolism compared to ginsenosides known to have conventional lipid metabolic efficacy.

In one embodiment, the present disclosure may provide a composition having a remarkably excellent efficacy for controlling cholesterol compared to ginsenosides known to have conventional cholesterol metabolic efficacy.

In one embodiment, the present disclosure may comprise the ginsenoside, a pharmaceutically acceptable salt thereof, a hydrate thereof, or a solvate thereof, thereby providing a composition for inhibiting differentiation of adipocytes. In one embodiment, the present disclosure may comprise the ginsenoside, a pharmaceutically acceptable salt thereof, a hydrate thereof, or a solvate thereof, thereby providing a composition for inhibiting the accumulation of fat in the body. In one embodiment, the present disclosure may prevent or treat obesity as well as related diseases by inhibiting differentiation of adipocytes or accumulation of fat.

In one embodiment, the present disclosure may provide a composition having a remarkably excellent anti-obesity efficacy compared to ginsenosides known to have conventional anti-obesity efficacy.

In one embodiment, the active ingredient may expand blood vessels to increase blood flow and promote blood circulation. In addition, as an embodiment, the active ingredient may prevent or delay aging of blood vessels by promoting growth and regeneration of vascular endothelial cells. Blood circulation may be improved by preventing blood vessels from losing elasticity and restoring the inhibited blood flow to a normal state. As a result, the composition according to an embodiment of the present disclosure may prevent or improve blood circulation-related diseases, for example, neck and shoulder stiffness, hands and feet numbness, cold hands and feet, lower body edema, or the like. In addition, the composition according to an embodiment of the present disclosure may also provide an effect of improving the color or skin tone of the skin by expanding capillaries and promoting blood circulation when applied to the skin.

In one embodiment, the present disclosure may provide a composition having a remarkably excellent blood circulation improving efficacy compared to ginsenosides known to have conventional blood circulation improving efficacy.

In one embodiment, the present disclosure may contain the active ingredient in an amount of 0.0001 to 99.9% by weight based on the total weight of the composition. Specifically, as one embodiment, the composition may contain the active ingredient in an amount of at least 0.0001% by weight, at least 0.0005% by weight, at least 0.001% by weight, at least 0.01% by weight, at least 0.1% by weight, at least 1% by weight, at least 2% by weight, at least 3% by weight, at least 4% by weight, at least 5% by weight, at least 6% by weight, at least 7% by weight, at least 8% by weight, at least 9% by weight, at least 10% by weight, at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 80% by weight, at least 85% by weight, at least 90% by weight, at least 95% by weight, or at least 99.9% by weight based on the total weight of the composition, but is not limited to the above range. In addition, as one embodiment, the composition may contain the active ingredient in an amount of 100% or less by weight, 99% or less by weight, 95% or less by weight, 90% or less by weight, 85% or less by weight, 80% or less by weight, 75% or less by weight, 70% or less by weight, 65% or less by weight, 60% or less by weight, 55% or less by weight, 50% or less by weight, 45% or less by weight, 40% or less by weight, 35% or less by weight, 30% or less by weight, 25% or less by weight, 20% or less by weight, 15% or less by weight, 10% or less by weight, 9% or less by weight, 8% or less by weight, 7% or less by weight, 6% or less by weight, 5% or less by weight, 4% or less by weight, 3% or less by weight, 2% or less by weight, 1% or less by weight, 0.5% or less by weight, 0.1% or less by weight, 0.01% or less by weight, 0.001% or less by weight or 0.0005% or less by weight based on the total weight of the composition, but is not limited to the above range.

The composition according to embodiments of the present disclosure may be a composition for external skin application comprising the active ingredient.

As used herein, "skin" means the tissue covering the body surface of an animal and is used in the broadest sense, comprising not only the tissue that covers the face or body but also the scalp and hair.

The composition according to the embodiments of the present disclosure may be a food composition comprising the active ingredient.

For example, it may be processed into functional foods such as fermented milk, cheese, yogurt, juice, probiotic and health food containing the active ingredient, and may be used in the form of various other food additives. In one embodiment, the composition may be a composition for health food. In one embodiment, the composition for health food may be formulated into pills, capsules, tablets, granules, caramels, drinks, or the like. In another embodiment, the composition may be processed in the form of liquid, powder, granules, tablets, tea bags, or the like. The composition may be administered by various methods such as simple drinking, injection administration, spray administration or squeeze administration, or the like. The composition may contain other components that can give a synergistic effect to the main effect within a range that does not impair the main effect of the present disclosure. For example, it may further comprise additives such as perfumes, pigments, fungicides, antioxidants, preservatives, moisturizers, thickeners, inorganic salts, emulsifiers and synthetic polymer materials, or the like for improving the physical properties. In addition, the composition may further comprise auxiliary components, comprising water-soluble vitamins, oil-soluble vitamins, polymer peptides, polysaccharides and seaweed extracts. The above components may be suitably selected and mixed by those skilled in the art depending on the formulation or purpose of use and may be added in an amount selected within the range that does not impair the object and effect of the present disclosure. For example, the above components may be added in an amount of 0.0001 to 99.9% by weight based on the total weight of the composition. In one embodiment, the dosage of the food composition may vary depending on the judgement such as age, sex, and weight of the subject, the specific disease or pathology of the subject, the severity of the disease or pathologic state, the route of administration, or the like. The determination of dosage based on these factors is within the level of those skilled in the art. For example, the dosage may be at least 0.05 mg/kg/day or at least 1 mg/kg/day, and may be at most 10 g/kg/day, at most 100 mg/kg/day or at most 10 mg/kg/day. However, the dosage does not limit the scope of the present specification in any way.

The composition according to the embodiments of the present disclosure may be a pharmaceutical composition comprising the active ingredients. The pharmaceutical composition may further comprise a pharmaceutical adjuvant such as antiseptic, stabilizer, hydrating agent, emulsifying accelerator, salt and/or buffer for controlling osmotic pressure, etc. or other therapeutically useful substance.

In one embodiment, the pharmaceutical composition may be a formulation for oral administration. The formulation for oral administration may comprise, for example, tablet, pill, hard or soft capsule, liquid, suspension, emulsion, syrup, powder, dust, granule, pellet, or the like. These formulations may comprise, in addition to the active ingredient, a surfactant, a diluent (e.g., lactose, dextrose, sucrose, mannitol, sorbitol, cellulose or glycine) or a lubricant (e.g., silica, talc, stearic acid and magnesium or calcium salt thereof, or polyethylene glycol). The tablet may comprise a binder such as magnesium aluminum silicate, starch paste, gelatin, tragacanth, methyl cellulose, sodium carboxymethyl cellulose and polyvinylpyrrolidone, and may occasionally comprise a pharmaceutical additive such as a disintegrant, e.g. starch, agar, alginic acid or a sodium salt thereof, an absorbent, a colorant, a flavor, a sweetener, or the like. The tablet may be prepared according to the commonly employed mixing, granulation or coating method.

In one embodiment, the pharmaceutical composition may be a formulation for parenteral administration, and the formulation for parenteral administration may be rectal, topical, subcutaneous, transdermal dosage form. The formulation for parenteral administration may comprise, for example, injection, drop, ointment, lotion, gel, cream, spray, suspension, emulsion, suppository, patch, etc., but is not limited thereto.

In one embodiment, the dose of the pharmaceutical composition may be varied with the age, sex and body weight of a subject to be treated, particular disease or pathological condition be treated, severity of the disease or pathological condition, administration route and the judgment of a prescriber. Determination of the dose considering these factors is within the level of those skilled in the art. For example, the dosage may be at least 0.05 mg/kg/day or at least 1 mg/kg/day, and may be at most 10 g/kg/day, at most 100 mg/kg/day or at most 10 mg/kg/day. However, the dosage does not limit the scope of the present specification in any way.

The composition according to the embodiments of the present disclosure may be a cosmetic composition comprising the active ingredients.

In one embodiment, the composition may be formulated by comprising a cosmetologically or dermatologically allowable medium or base. It may be provided in any topically applicable form comprising, for example, solutions, gels, anhydrous solids or pastes, oil-in-water emulsions, suspensions, microemulsions, microcapsules, microgranules, ionic (liposomes) or non-ionic vesicular dispersions, creams, skin lotions, milk lotions, powders, ointments, sprays and concealing sticks. In addition, the composition may also be used in the form of foam or an aerosol composition further containing compressed propellants. Such compositions may be prepared by a method commonly employed in the pertinent field.

Hereinafter, the present disclosure will be described in detail with reference to examples, comparative examples and test examples. These are only presented by way of example only to more specifically describe the present disclosure, and it is obvious to those skilled in the art that the scope of the present disclosure is not limited by these examples, comparative examples and test examples.

All experimental values below represent the average of values obtained by repeating experiments three or more times, and standard deviation (SD) is indicated by error bars. p values were calculated by one-way ANOVA and Dunnett test, and p values less than 0.05 were considered statistically significant.

[Example 1] Isolation of Ginsenosides

Fraction 5.5 kg of *Ginseng* seed (seeds of *Panax Ginseng*) was finely ground in a mixer to make a powder form, extracted with methanol, and then fractionated step by step using n-hexane, ethyl acetate, n-butanol, and the like. Lipids were mostly removed by n-hexane, and the lipids remaining in the ethyl acetate fraction were suspended in methanol:water=1:1 (v/v), stored in the freezer overnight, and then only the supernatant was taken. The lipids were removed once more using a centrifuge. 2.61 g of ethyl acetate fraction and 114.64 g of n-butanol fraction thus pretreated were fractionated through column and HPCCC (High Performance Counter-Current Chromatography) as follows.

Fraction Using Columns of n-Butanol Fractions and HPCCC 114.64 g of n-butanol fraction was fractionated by MPLC, and the solvent used then was n-hexane/ethyl acetate=10:1→5:1→1:1→CHCl$_3$/MeOH=10:1→5:1 (v/v) and flow rate was 50 mL/min. The above conditions were used to make a total of 12 subfractions, and the components contained in each fraction were separated again using HPCCC, HPLC (High-performance liquid chromatography), Sephadex LH-20 column, or the like. 16 compounds were investigated by identifying their structure using NMR (Nuclear magnetic resonance), UV (Ultraviolet rays), and MS (Mass spectrometry).

The 16 compounds isolated comprise ginsenoside Rg1 (compound 1), ginsenoside Rg2 (compound 2) and ginsenoside Re (compound 3), which are protopanaxatriol saponins; ginsenoside Rd (compound 4), ginsenoside Rb1 (compound 5) and ginsenoside Rb2 (compound 6), which are protopanaxadiol saponins; stigma-5-en-3-O-β-D-glucopyranoside (compound 7), stigma-5,24(28)-dien-3-O-β-D-glucopyranoside (compound 8) and stigma-5,22-dien-3-O-β-D-glucopyranoside (compound 9), which are sterol glycosides; (20S,24R)-6-O-β-D-glucopyranosyl(1→2)-β-D-glucopyranoside-dammar-3-one-20,24-epoxy-6a,12b,25-triol (compound 10), a novel compound that is first isolated from nature as a novel ginsenoside according to an embodiment of the present disclosure; phenethyl alcohol β-D-xylopyranosyl(1→6)-β-D-glucopyranoside (compound 12) and Eugenyl R-gentiobioside (compound 13), which are phenolic glycosides; isorhamnetin 3-O-β-D-glucopyranoside (compound 15), which is flavonoid; and adenosine (compound 11), uracil (compound 14) and tryptophan (compound 16), which are primary metabolites.

Figure 2:
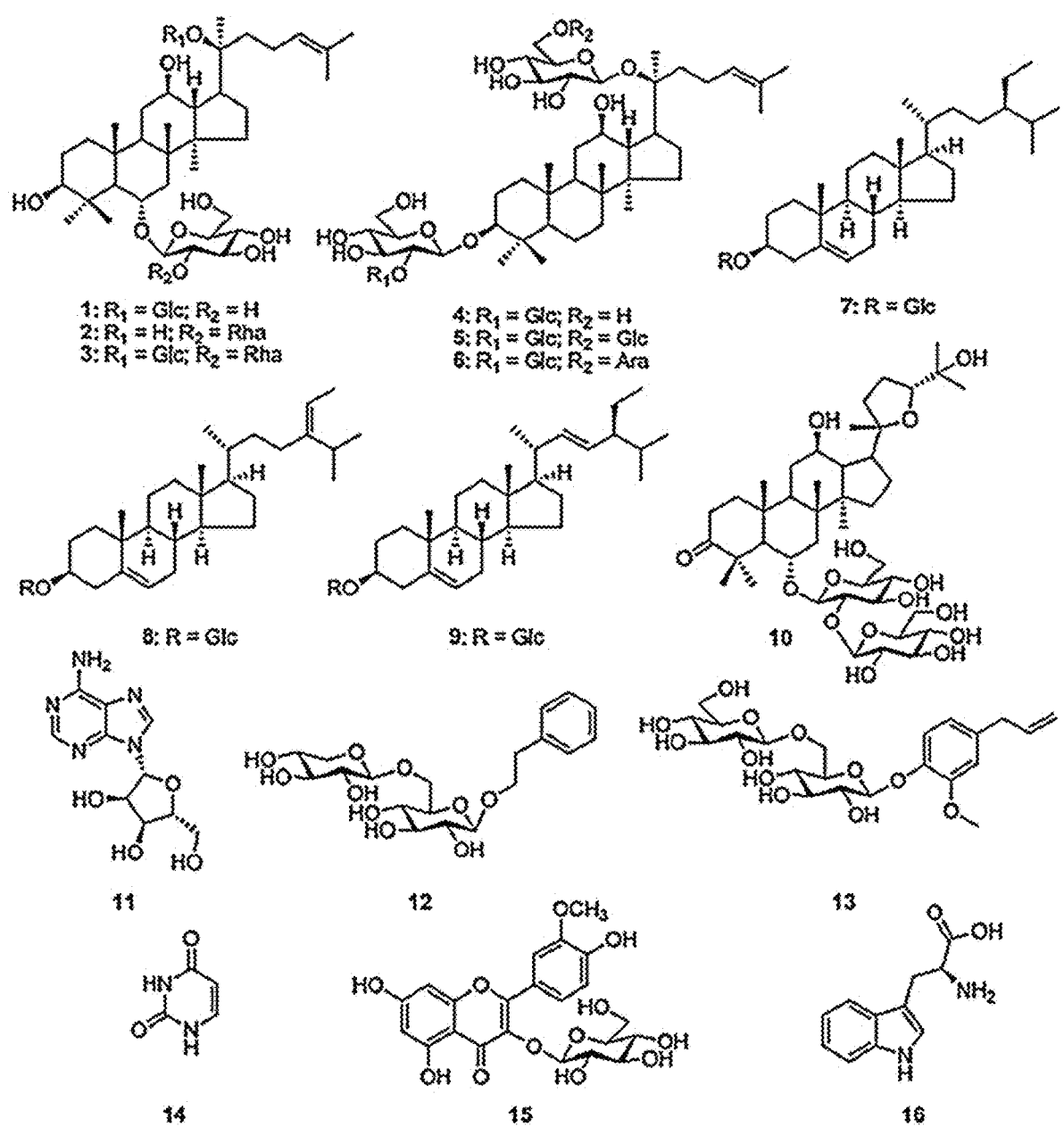
FIG. 2 is a diagram illustrating the chemical structures of 16 compounds fractionated from *Ginseng* seed extract.
Figure 3:
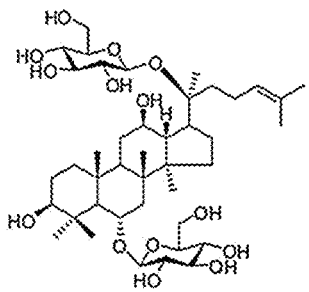
FIG. 3 is a diagram illustrating the spectroscopic evidence and structures of compounds 1 to 6 corresponding to the previously known ginsenosides among the compounds fractionated from *Ginseng* seed extract.
Figure 3:
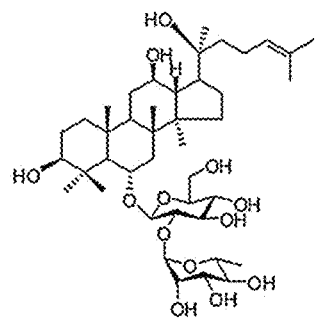
Figure 3:
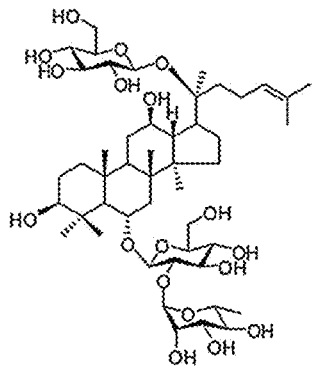
Figure 3:
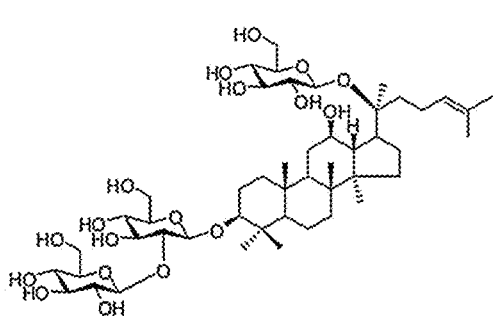
Figure 3:
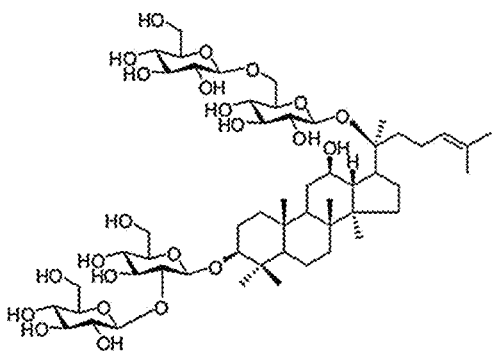
Figure 3:
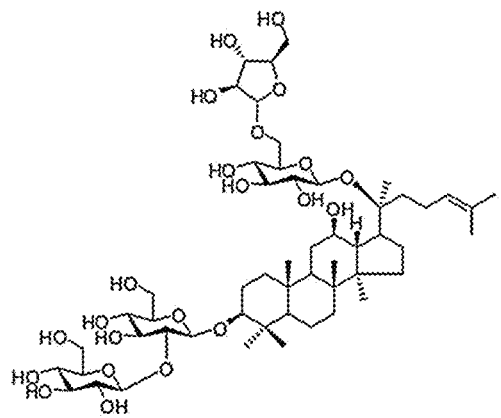
Figure 4:
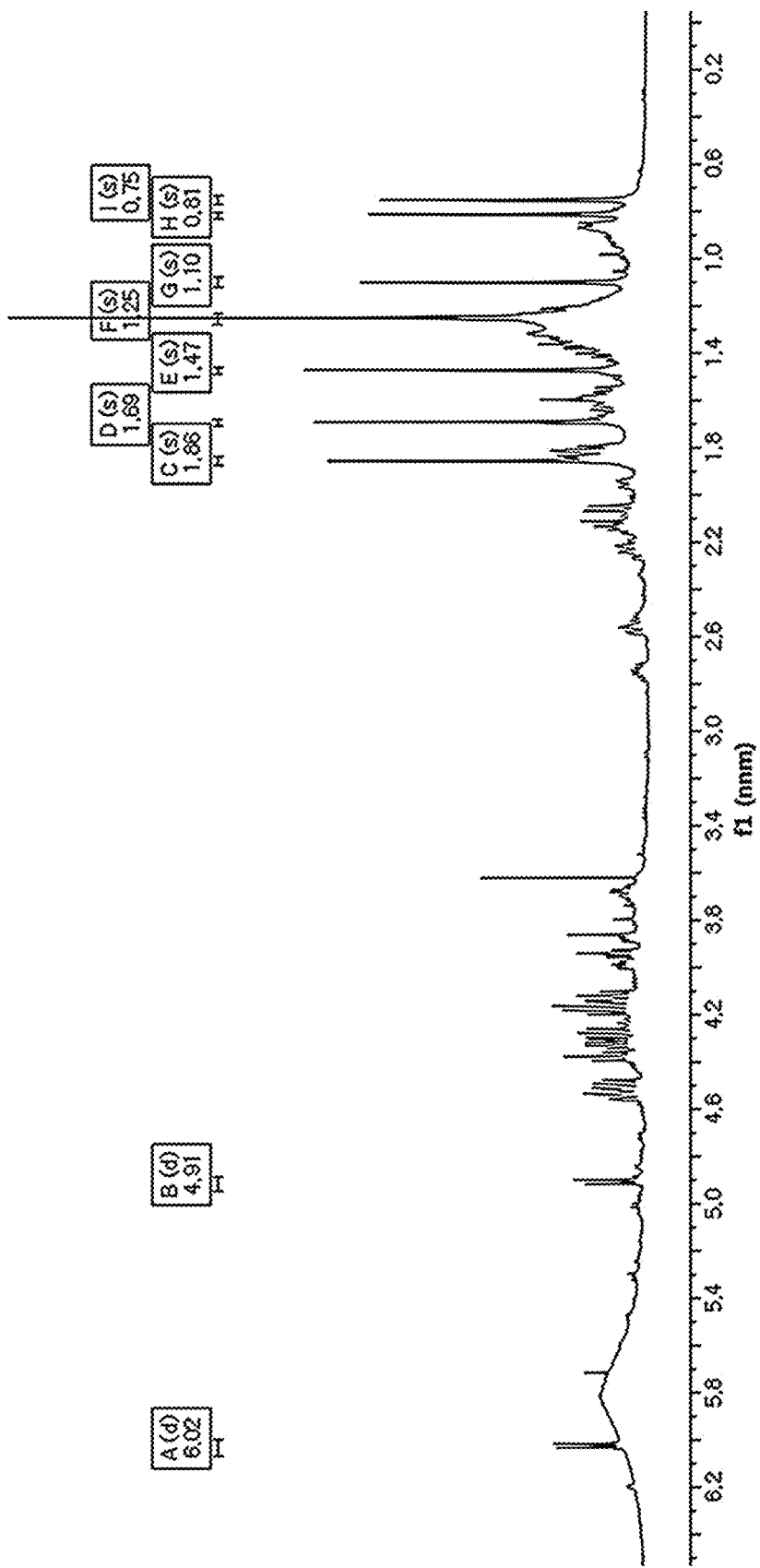
FIG. 4 is a diagram illustrating a 1H-NMR spectrum of compound 10 corresponding to the novel ginsenoside of the present disclosure among the compounds fractionated from *Ginseng* seed extract.
Figure 5:
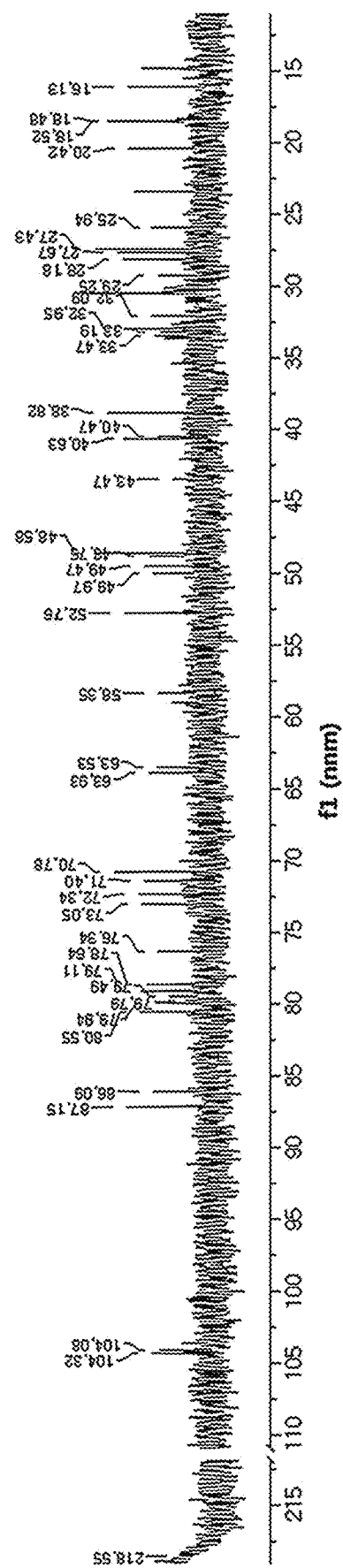
FIG. 5 is a diagram illustrating a $^{13}$C-NMR spectrum of compound 10 corresponding to the novel ginsenoside of the present disclosure among the compounds fractionated from *Ginseng* seed extract.
Figure 6:
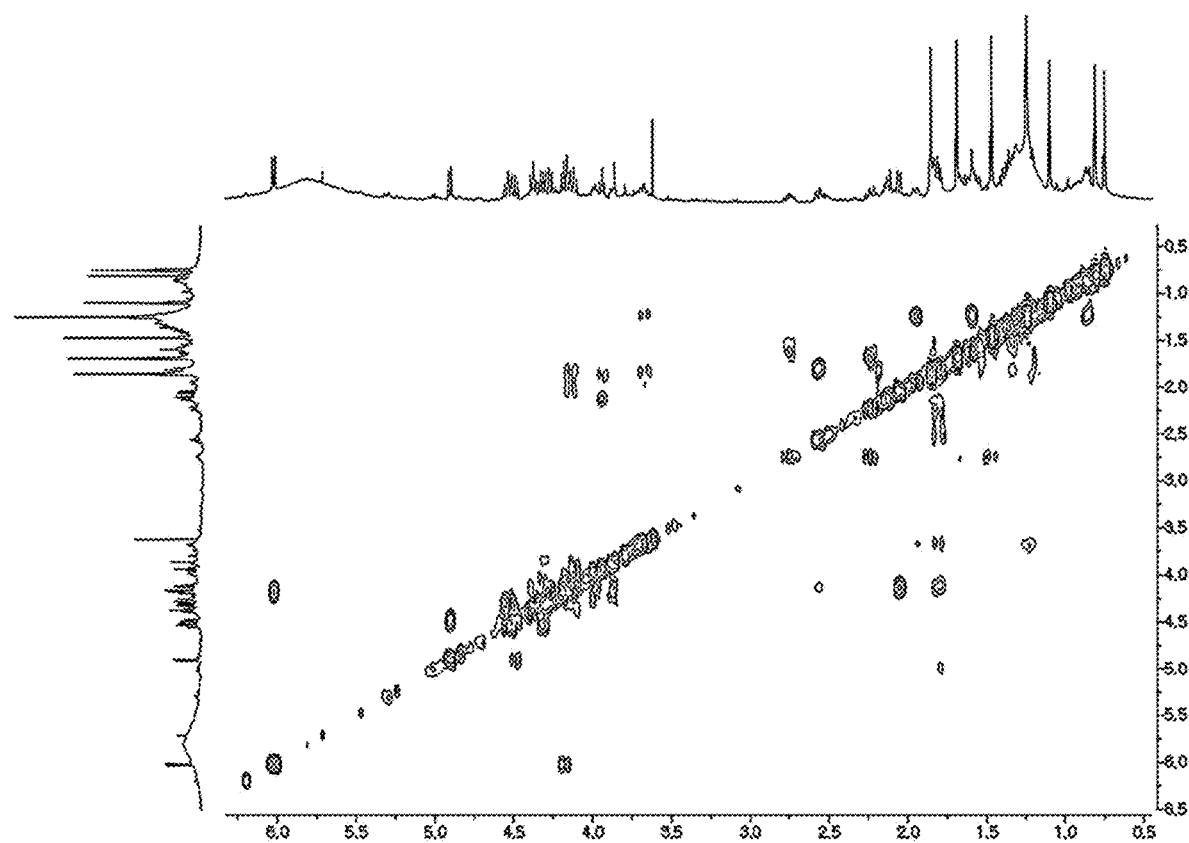
FIG. 6 is a diagram illustrating a COSY spectrum of compound 10 corresponding to the novel ginsenoside of the present disclosure among the compounds fractionated from *Ginseng* seed extract.
Figure 7:
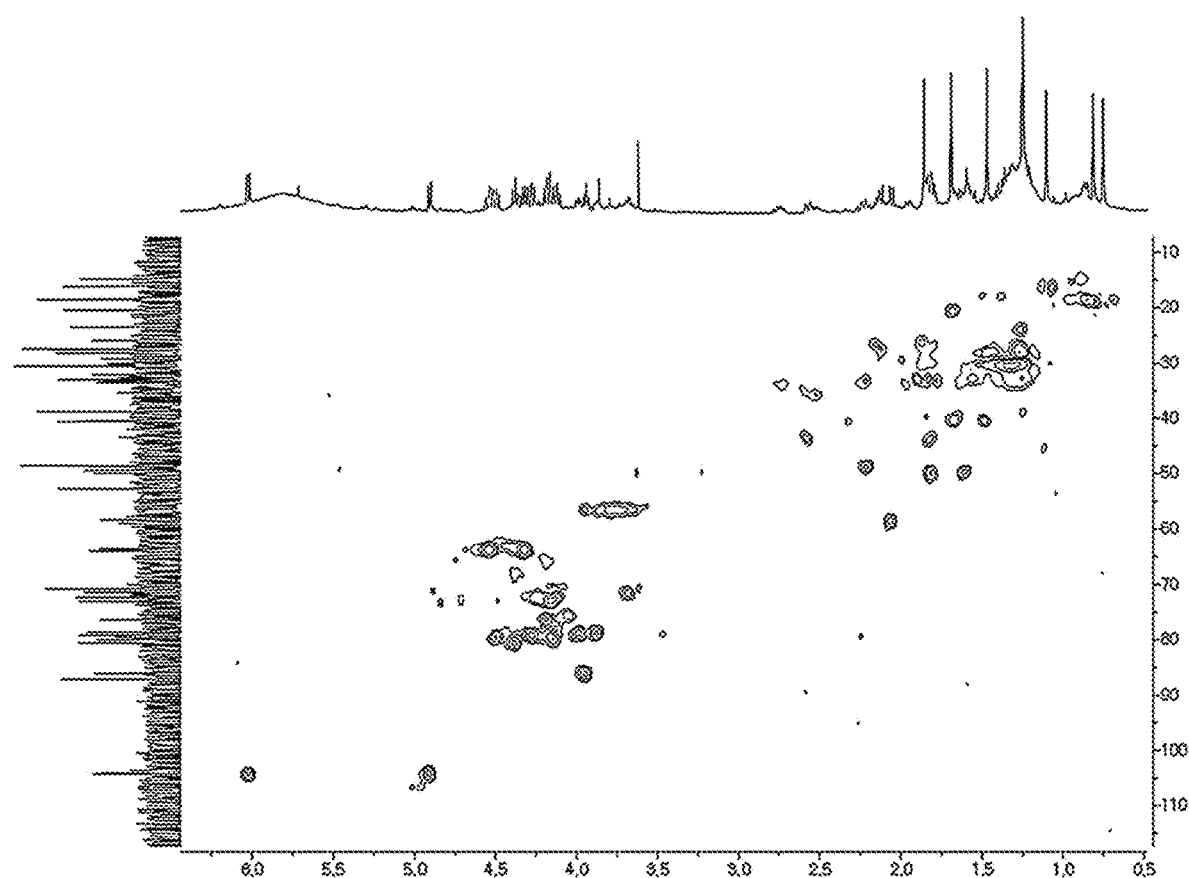
FIG. 7 is a diagram illustrating an HSQC spectrum of compound 10 corresponding to the novel ginsenoside of the present disclosure among the compounds fractionated from *Ginseng* seed extract.
Figure 8:
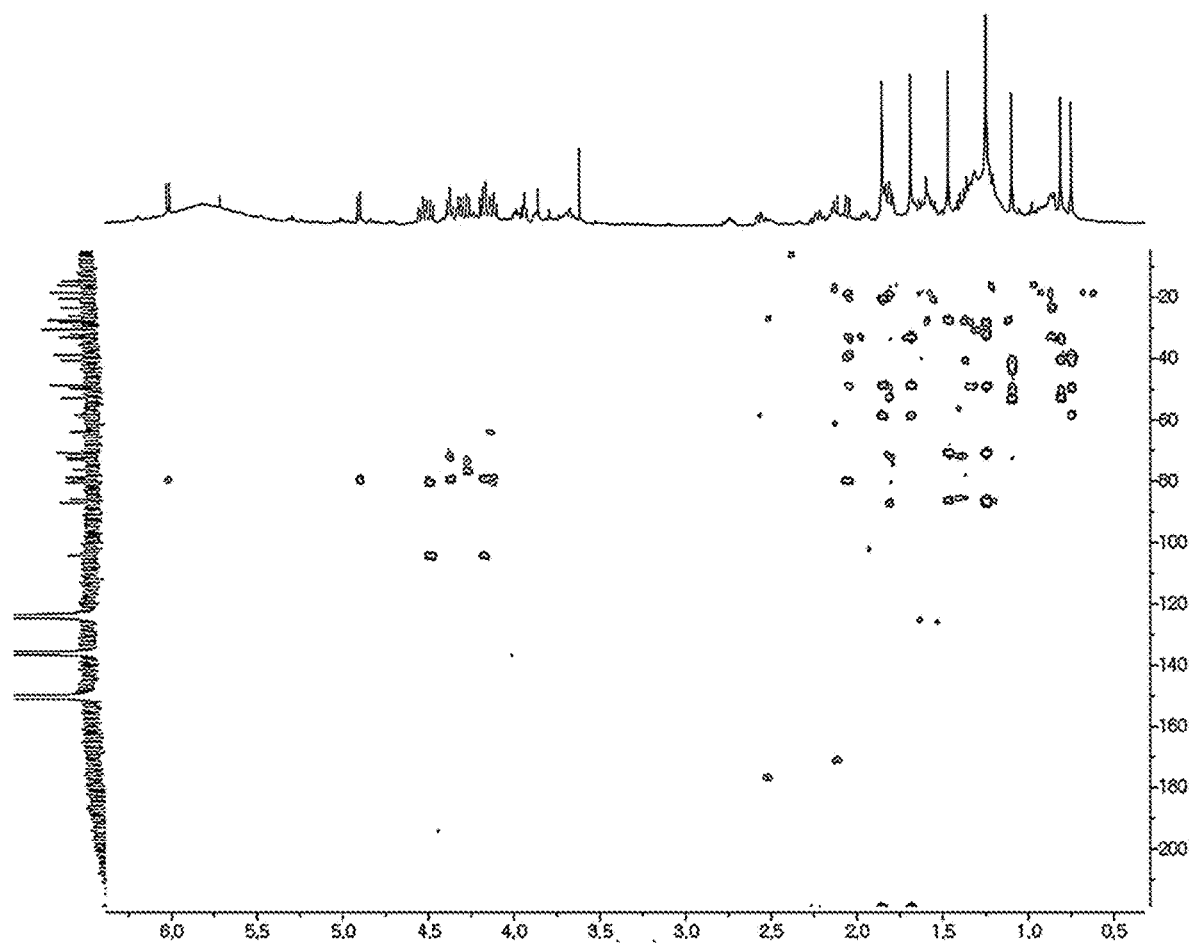
FIG. 8 is a diagram illustrating an HMBC spectrum of compound 10 corresponding to the novel ginsenoside of the present disclosure among the compounds fractionated from *Ginseng* seed extract.
Figure 9:
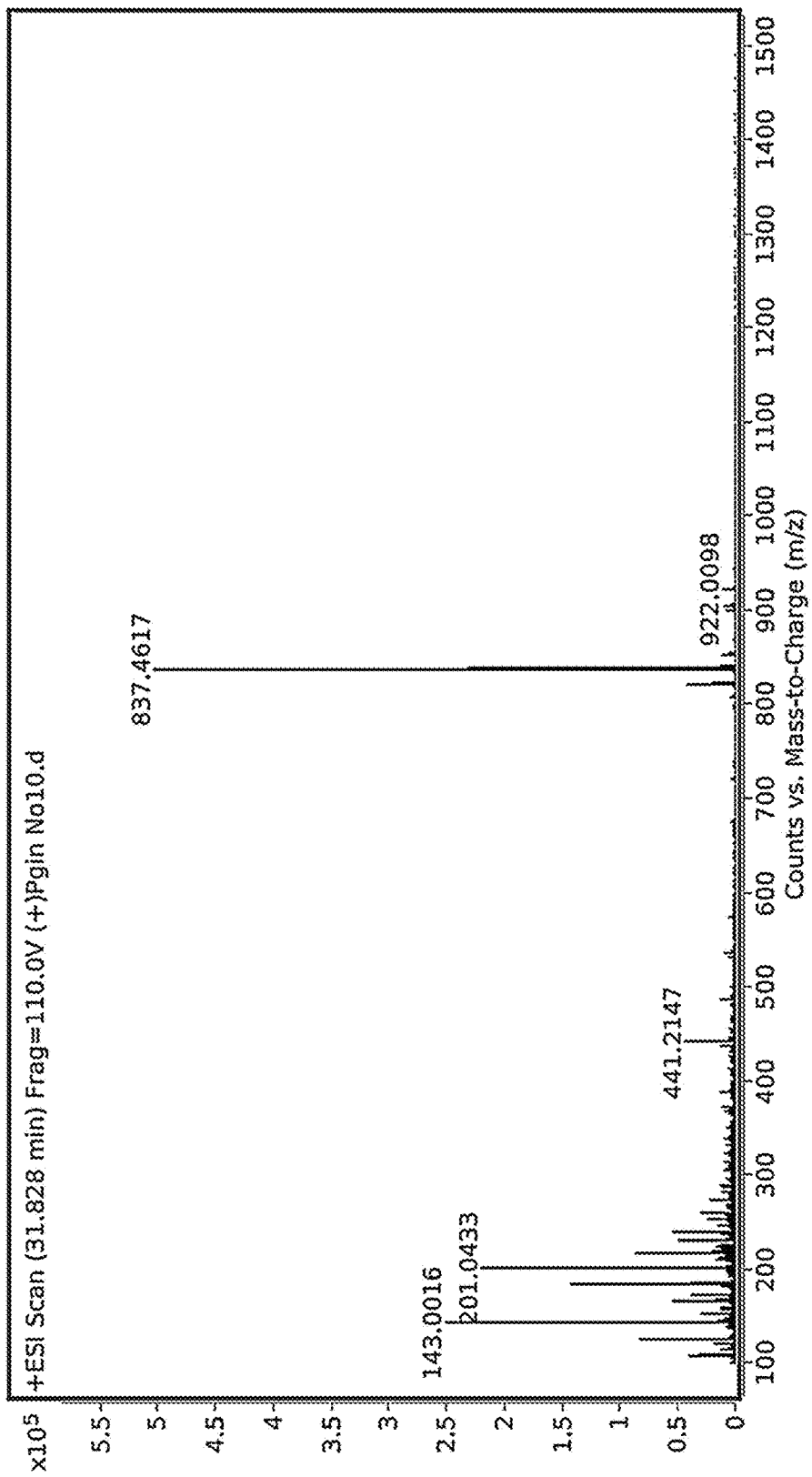
FIG. 9 is a diagram illustrating an MS spectrum of compound 10 corresponding to the novel ginsenoside of the present disclosure among the compounds fractionated from *Ginseng* seed extract.
Figure 10:
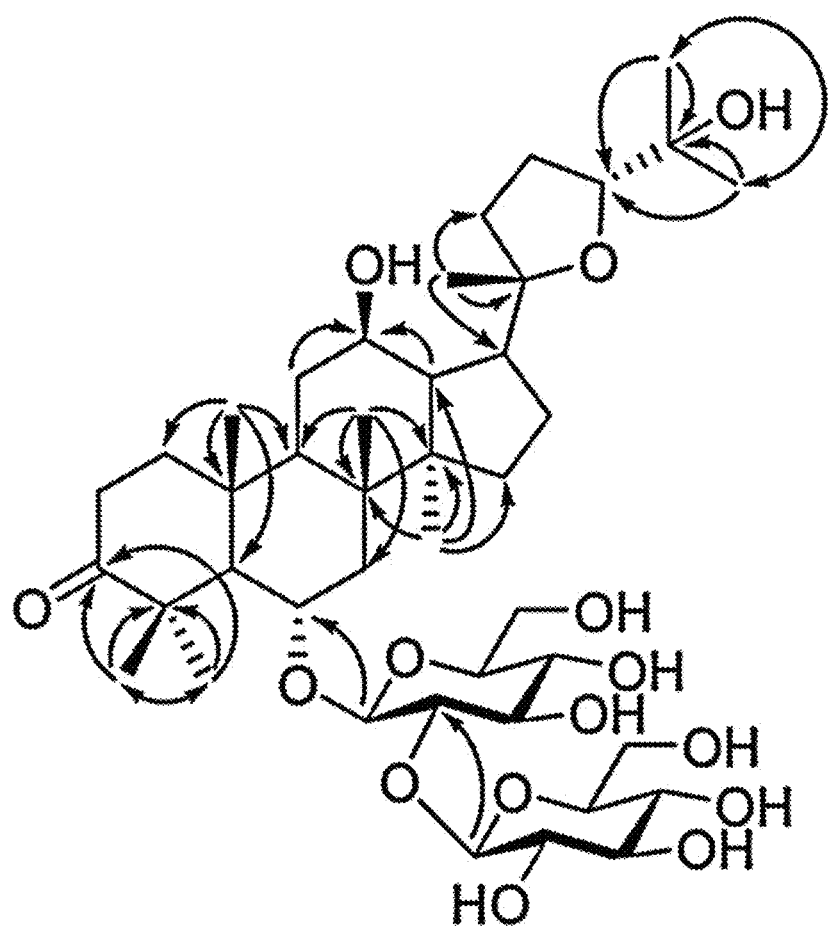
FIG. 10 is a diagram illustrating the core HMBC correlation of compound 10 corresponding to the novel ginsenoside of the present disclosure among the compounds fractionated from *Ginseng* seed extract.

An isolation process of a novel ginsenoside according to an embodiment of the present disclosure corresponding to compound 10 above is shown in FIG. 1. The chemical structures of the 16 compounds are shown in FIG. 2, and spectroscopic evidence and chemical structures of the conventionally known ginsenoside compounds 1-6 among the above compounds are separately shown in FIG. 3.

Compound 10 was isolated as a white amorphous powder showing the molecular formula of $C_{42}H_{70}O_{15}$ based on the sodiated pseudomolecular ion peak at m/z 837.4617 [(M+Na)$^+$ calcd. 837.4612] in the cationic ESI-Q-TOF-MS (Electrospray Ionization-Quadrupole-Time-of-flight mass spectrometry) spectrum. The 1H NMR spectrum of the compound 10 contained 8 methyl resonances in [$δ_H$ 1.86 (3H, s, H-28), 1.69 (3H, s, H-29), 1.47 (3H, s, H-27), 1.25 (6H, s, H-21, 26), 1.10 (3H, s, H-18), 0.81 (3H, s, H-30), 0.75 (3H, s, H-19)]. In addition, two pairs of signals corresponding to the anomeric protons and carbon atoms at the two sugar residues were detected at $δ_H$ 6.02 (1H, d, J=7.8, H-2")/$δ_C$ 104.08 (C-1') and $_H$4.91 (1H, d, J=7.7, H-1')/$δ_C$ 104.32 (C-1"). $^{13}$C NMR and heteronuclear single quantum correlation (HSQC) spectra revealed 42 carbon signals. Apart from the two sugar residues above, the aglycone of compound 10 had eight methylenes, four methines, three oxygen-containing methines [$δ_C$ 79.79 (C-6), 71.40 (C-12) and 86.09 (C-24)], five quaternary carbon atoms, two oxygenated quaternary carbon atoms [$δ_C$ 87.15 (C-20) and 70.78 (C-25)], and eight methyl groups and carbonyl carbon [$δ_C$ 218.85 (C-3)]. As a result of thorough interpretation of $^1$H and $^{13}$C NMR data, the aglycone of compound 10 was found to be superimposed on pseudoginsengenin R1 [(20S,24R)-dammar-3-one-20,24-epoxy-6α,12β,25-triol])]. The absolute configuration of C-20 in compound 10 was deduced from S to chemical shift of C-21 ($δ_C$ 27.67), and the 24R configuration was determined by chemical shift of C-24 ($δ_C$ 86.09) as previously disclosed. Both sugar units were turned out to be β-D-glucopyranosyl residues from the coupling constants of the anomeric protons at $^1$H NMR spectra and 12 carbon resonances, together with acid hydrolysis data and gas chromatography (GC) analysis results. A glycoside linkage was determined by heteronuclear multiple bond correlation (HMBC) which showed cross peaks at $δ_H$ 6.02 (H-1")/$δ_C$ 79.49 (C-2') and $δ_H$ 4.91 (H-1')/$δ_C$ 79.79 (C-6), and it was demonstrated that 2-O-(β-D-glucopyranosyl)-β-D-glucopyranosyl residues were linked to C-6 of aglycone at pseudoginsengenin R1. Each of the analytical spectra of the compound 10 and the core HBMC correlation are shown in FIGS. 4 to 10.

In the above analysis results, it was determined that the chemical structure of compound 10 was (20S,24R)-6-O-β-D-glucopyranosyl(1→2)-β-D-glucopyranoside-dammar-3-one-20,24-epoxy-6a,12b,25-triol, and named pseudoginsenoside RT8 (PG-RT$_8$).

Among the ginsenosides isolated from the Ginseng seed extract, ginsenoside Rg1 (compound 1), ginsenoside Rg2 (compound 2) and ginsenoside Re (compound 3), which are PPT (ProtoPanaxTriol) based ginsenosides, comprise three hydroxyl groups in the ginsenoside backbone. Ginsenoside Rd (compound 4), ginsenoside Rb1 (compound 5), and ginsenoside Rb2 (compound 6), which are PPD (ProtoPanax Diol) based ginsenosides, comprise two hydroxyl groups in the ginsenoside backbone. On the other hand, compound 10, which is a newly isolated and identified ginsenoside in the present disclosure, has a PPT-based backbone, but the terminal hydroxyl group of the backbone is ketone, and there is a structural difference in that the linear chain of ginsenoside is cyclized with a furan ring.

In the present disclosure, the molecular formula of the newly isolated and identified compound 10 was $C_{42}H_{70}O_{15}$, ESI-Q-TOF-MS, m/z was 837.4617 [M+Na]$^+$, and 1H, $^{13}$C-NMR spectra are shown in the following table.

TABLE 1

| Position | 13C-NMR | 1H-NMR |
|---|---|---|
| 1 | 40.63 | 1.67 (1H, H-1a)$^a$, 1.49 (1H, H-1b)$^a$ |
| 2 | 33.61 | 2.23 (1H, H-2a)$^a$, 1.78 (1H, H-2b)$^a$ |
| 3 | 218.85 | — |
| 4 | 48.58 | — |
| 5 | 58.35 | 2.06 (1H, d, j = 10.6 Hz, H-5) |
| 6 | 79.79 | 4.15 (1H, H-6)$^a$ |
| 7 | 43.47 | 2.57 (1H, H-7a)$^a$, 1.82 (1H, H-7b)$^a$ |
| 8 | 40.47 | — |
| 9 | 49.47 | 1.60 (1H, H-9)$^a$ |
| 10 | 38.82 | — |
| 11 | 33.47 | 2.22 (1H, H-11a)$^a$, 1.32 (1H, H-11b)$^a$ |
| 12 | 71.40 | 3.68 (1H, td, j = 10.6, 4.5 Hz, H-12) |
| 13 | 49.97 | 1.81 (1H, H-13)$^a$ |
| 14 | 52.76 | — |
| 15 | 33.19 | 1.64 (1H, H-15a)$^a$, 1.26 (1H, H-15b)$^a$ |
| 16 | 25.94 | 2.17 (1H, H-16a)$^a$, 1.87 (1H, H-16b)$^a$ |
| 17 | 48.75 | 2.21 (1H, H-17)$^a$ |
| 18 | 16.13 | 1.10 (3H, s, H-18) |
| 19 | 18.48 | 0.75 (3H, s, H-19) |
| 20 | 87.15 | — |
| 21 | 27.67 | 1.25 (3H, s, H-21) |
| 22 | 32.09 | 1.60 (1H, H-22a)$^a$, 1.37 (1H, H-22b)$^a$ |
| 23 | 29.25 | 1.82 (1H, H-23a)$^a$, 1.25 (1H, H-23b)$^a$ |
| 24 | 86.09 | 3.94 (1H, t, j = 7.5 Hz, H-24) |
| 25 | 70.78 | — |
| 26 | 27.43 | 1.25 (3H, s, H-26) |
| 27 | 28.18 | 1.45 (3H, s, H-27) |
| 28 | 32.95 | 1.86 (3H, s, H-28) |
| 29 | 20.42 | 1.69 (3H, s, H-29) |
| 30 | 18.52 | 0.81 (3H, s, H-30) |

$^a$peak was overlapped

TABLE 2

| Position | 13C-NMR | 1H-NMR |
|---|---|---|
| 6-O-Glc | | |
| 1' | 104.08 | 4.91 (1H, d, j = 7.7 Hz, H-1') |
| 2' | 79.49 | 4.48 (1H, m, H-2') |
| 3' | 80.55 | 4.38 (1H, m, H-3') |
| 4' | 73.05 | 4.16 (1H, m, H-4') |
| 5' | 79.94 | 4.15 (1H, m, H-5') |
| 6' | 63.53 | 4.54 (1H, m, H-6'a), 4.32 (1H, m, H-6'b) |
| 2'-O-Glc | | |
| 1" | 104.32 | 6.02 (1H, d, j = 7.8 Hz, H-1") |
| 2" | 76.34 | 4.18 (1H, m, H-2") |
| 3" | 78.64 | 3.99 (1H, m, H-3") |
| 4" | 72.34 | 4.12 (1H, m, H-4") |
| 5" | 79.11 | 4.27 (1H, m, H-5") |
| 6" | 63.93 | 4.54 (1H, m, H-6"a), 4.32 (1H, m, H-6"b) |

[Test Example 1] Comparison of Sugar Digestive Enzyme Activity Inhibitory Efficacy In order to compare the blood sugar inhibitory effects of ginsenosides isolated from the Ginseng seed extract, the inhibitory effect of the polysaccharide digestive enzyme was evaluated as follows.

As a polysaccharide degrading enzyme, pancreatic α-amylase and α-glucosidase were purchased from Sigma, and the enzyme activity of novel ginsenoside GS #10, which is an example of the present disclosure, isolated from Ginseng seed extract and ginsenosides GS #01-GS #06, which are comparative examples of the present disclosure, was measured. In order to measure α-amylase activity, enzyme solution was prepared by dissolving BSA 0.1 g, 0.01 g/L $NaN_3$, α-amylase 0.2857 g in 50 mL of PBS (phosphate buffered saline), and 5 mM of p-nitrophenyl-α-D-maltopentoglycoside was dissolved in another PBS to make a substrate solution. 0.1 mL of the test substance was added to 0.5 mL of the enzyme solution, and then the initial absorbance was measured at 405 nm. After adding 0.5 mL of the substrate solution and reacting it for 5 minutes, the absorbance was measured again. The change in enzyme activity was measured by the difference in absorbance between the two reactions. The method for measuring α-glucosidase activity is the same as the method for measuring α-amylase activity, and differs only in α-glucosidase and substrate (p-nitrophenyl-α-D-glucopyranoside). As a positive control to observe the inhibition of enzyme activity, acarbose, which is an α-amylase inhibitor and α-glucosidase inhibitor derived from wheat seed sold by Sigma, was used.

Figure 11:
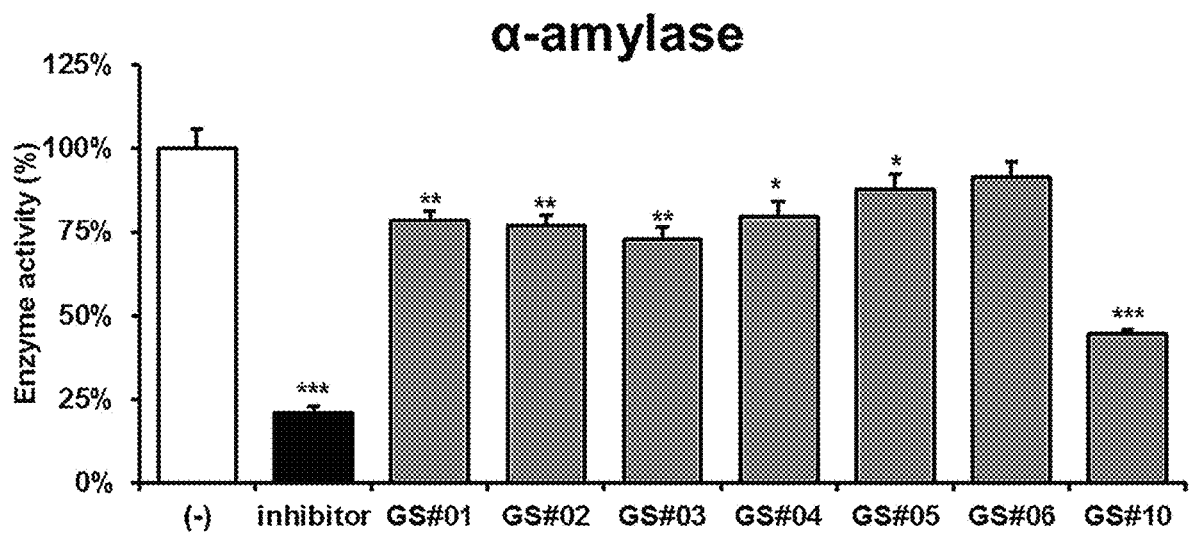
FIG. 11 is a diagram showing a comparison of the degree of inhibition of α-amylase enzyme activity of GS #10 corresponding to the novel ginsenoside of the present disclosure isolated from *Ginseng* seed extract and ginsenosides GS #01-GS #06 which are comparative examples of the present disclosure. (* $P<0.001$ vs. (−),  $P<0.01$ vs. (−), * $P<0.05$ vs. (−))
Figure 12:
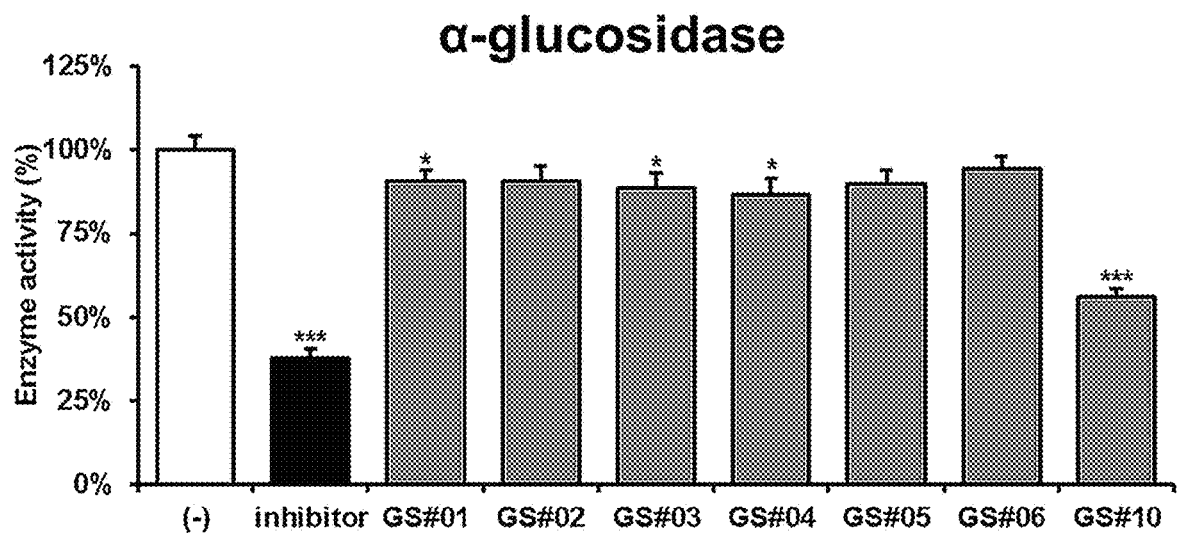
FIG. 12 is a diagram showing a comparison of the degree of inhibition of α-glucosidase enzyme activity of GS #10 corresponding to the novel ginsenoside of the present disclosure isolated from *Ginseng* seed extract and ginsenosides GS #01-GS #06 which are comparative examples of the present disclosure. (*** $P<0.001$ vs. (−), * $P<0.05$ vs. (−))

The α-amylase activity is shown in FIG. 11, and the α-glucosidase activity is shown in FIG. 12. In the case of α-amylase activity, all except GS #06 showed significant activity inhibitory effect. Among them, in particular, the novel ginsenoside GS #10, which is an example of the present disclosure, showed the most excellent α-amylase activity inhibitory effect. In the case of α-glucosidase, GS #05, GS #06 showed no activity inhibitory effect, and GS #01-GS #04 also showed a weaker degree of enzyme activity inhibition compared to α-amylase. However, since the novel ginsenoside GS #10, which is an example of the present disclosure, still showed high inhibitory effect on α-glucosidase activity, GS #10 was confirmed to have the most excellent inhibitory effect on glucose degradation. This is due to the chemical structural difference, which means that the novel ginsenoside PG-$RT_8$ of the present disclosure is far superior in hypoglycemic effect among Ginseng seed-derived ginsenosides, and is superior to previously known steroidal saponins.

[Test Example 2] Comparison of Glucose Transport Capacity

In order to determine the effect of ginsenosides isolated from the Ginseng seed extract on the body glycol-metabolism related to the blood sugar inhibitory effect, the effect of promoting cellular uptake of glucose in the blood was evaluated as follows.

Glucose transport is carried out by glucose transporters (GLUTs), and in order to increase glucose transport, the expression of glucose transporters and the location shift of the receptors to the cell membrane, i.e., cellular uptake of glucose, should be increased.

3T1-L1 adipocytes (ATCC) were purchased, and 10% bovine calf serum (Hyclone) and 1% penicillin/streptomycin (Sigma) were added to a Dulbecco's Modified Eagle's Medium (Sigma) and cultured in a 5% $CO_2$ culture medium. In order to differentiate preadipocyte cells into adipocytes, a culture plate was filled with cells and cultured for 48 hours. The cells were then replaced in a DMEM medium to which 10% fetal bovine serum (FBS) (Hyclone), 0.5 mM 3-isobutyl-1-methylxanthine (Sigma), 1 μM dexamethasone (Sigma), 5 μg/ml insulin (Sigma), and 1% penicillin/streptomycin were added and cultured for another 48 hours. Thereafter, the cells were further cultured for 14 days while being replaced in a medium containing 10% FBS, 5 μg/ml insulin, and 1% penicillin/streptomycin at two-day intervals to obtain fully differentiated adipocytes. Differentiated adipocytes were induced to be fasted using a low-glucose DMEM (Sigma) medium, and then glucose uptake ability was observed with a glucose uptake assay kit (abcam). As a positive control for measuring glucose uptake in blood, Metformin (Sigma; 10 μM), which is used as a diabetic therapeutic agent, was used, and novel ginsenoside GS #10, which is an example of the present disclosure, isolated from Ginseng seed extract and ginsenosides GS #01-GS #06, which are comparative examples of the present disclosure, were treated with 10 μM each. In addition, both insulin-dependent/independent glucose transport capacity was measured by treating insulin together, which may promote glucose uptake.

Figure 13:
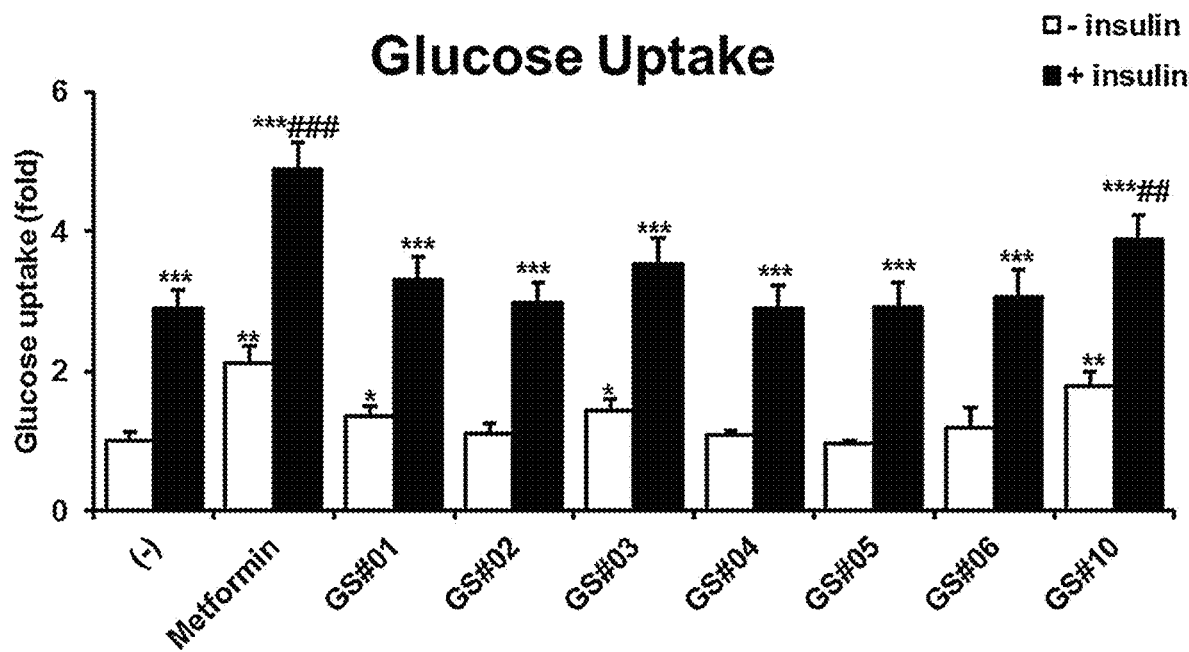
FIG. 13 is a diagram showing a comparison of the degree of glucose absorption promotion of GS #10 corresponding to the novel ginsenoside of the present disclosure isolated from *Ginseng* seed extract and ginsenosides GS #01-GS #06 which are comparative examples of the present disclosure. (* $P<0.001$ vs. −insulin (−),  $P<0.01$ vs. −insulin (−), * $P<0.05$ vs. insulin (−), ##$P<0.001$ vs. +insulin (−), ##$P<0.01$ vs. +insulin (−))

As a result, as shown in FIG. 13, among the ginsenosides isolated from Ginseng seed extract, only GS #01, GS #02, GS #03 and GS #10 showed statistically significant glucose transport promotion in the material-only treatment group (−insulin), and this effect was seen to further increase by insulin treatment (+insulin). In the case of the novel ginsenoside GS #10, which is an example of the present disclosure, as in metformin, the glucose transport is further increased as compared with the insulin-only treatment group (−) in combination therapy with insulin. Thus, it is considered a good material that may promote both insulin-dependent/independent glucose transport.

[Test Example 3] Comparison of Glyco-Metabolism Control Efficacy

The glycol-metabolism control efficacy of the novel ginsenoside GS #10, which is an example of the present disclosure, was compared with ginsenosides Rg1, Rg3 and Rb1 (purchased from Sigma), which are the red Ginseng index components as comparative examples of the present disclosure. The chemical structure of ginsenoside Rg3 of the comparative example of the present disclosure is as follows.

[Formula 2]

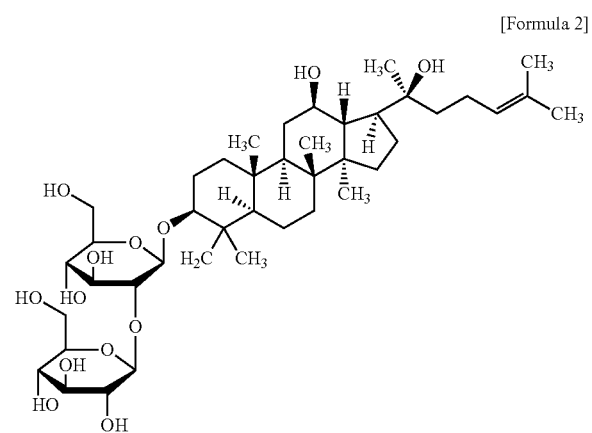

Experiments were carried out in the same manner as in Test Examples 1 and 2, wherein each ginsenoside was treated by 1, 10 µM, respectively.

Figure 14:
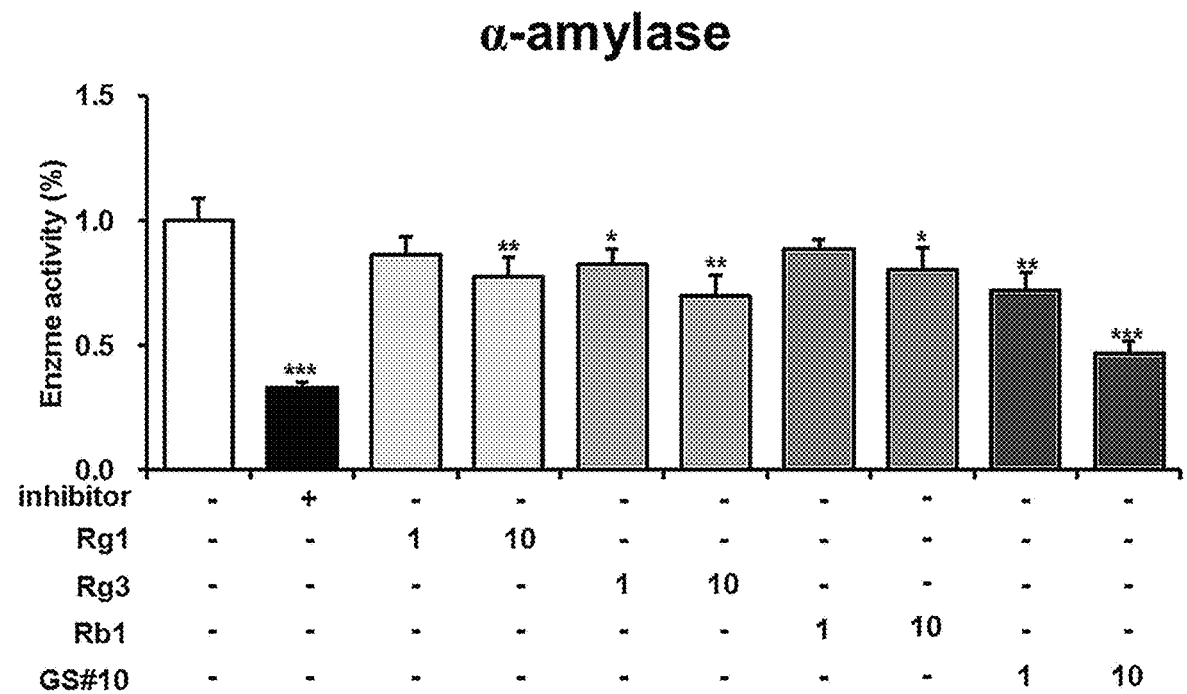
FIG. 14 is a diagram showing a comparison of the degree of inhibition of α-amylase enzyme activity of ginsenosides Rg1, Rg3 and Rb1 of the red *Ginseng* index component and GS #10 corresponding to the novel ginsenoside of the present disclosure. (* $P<0.001$ vs. (−),  $P<0.01$ vs. (−), * $P<0.05$ vs. (−))
Figure 15:
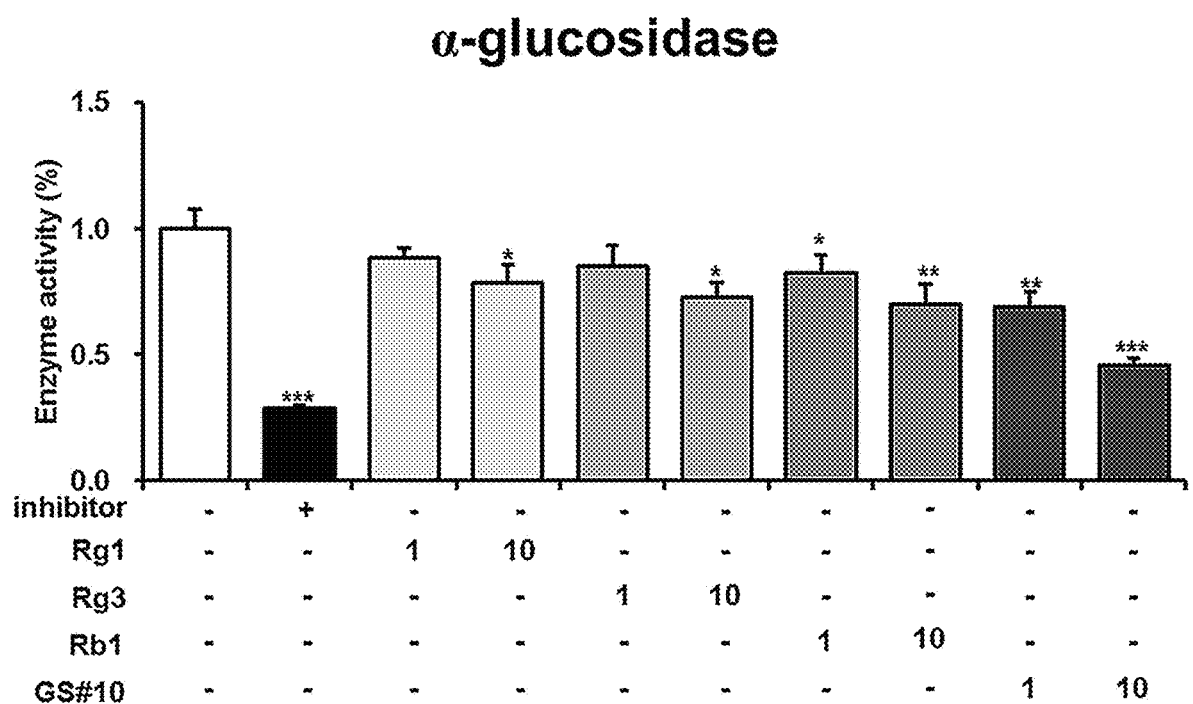
FIG. 15 is a diagram showing a comparison of the degree of inhibition of α-glucosidase enzyme activity of ginsenosides Rg1, Rg3 and Rb1 of the red *Ginseng* index component and GS #10 corresponding to the novel ginsenoside of the present disclosure. (* $P<0.001$ vs. (−),  $P<0.01$ vs. (−), * $P<0.05$ vs. (−))
Figure 16:
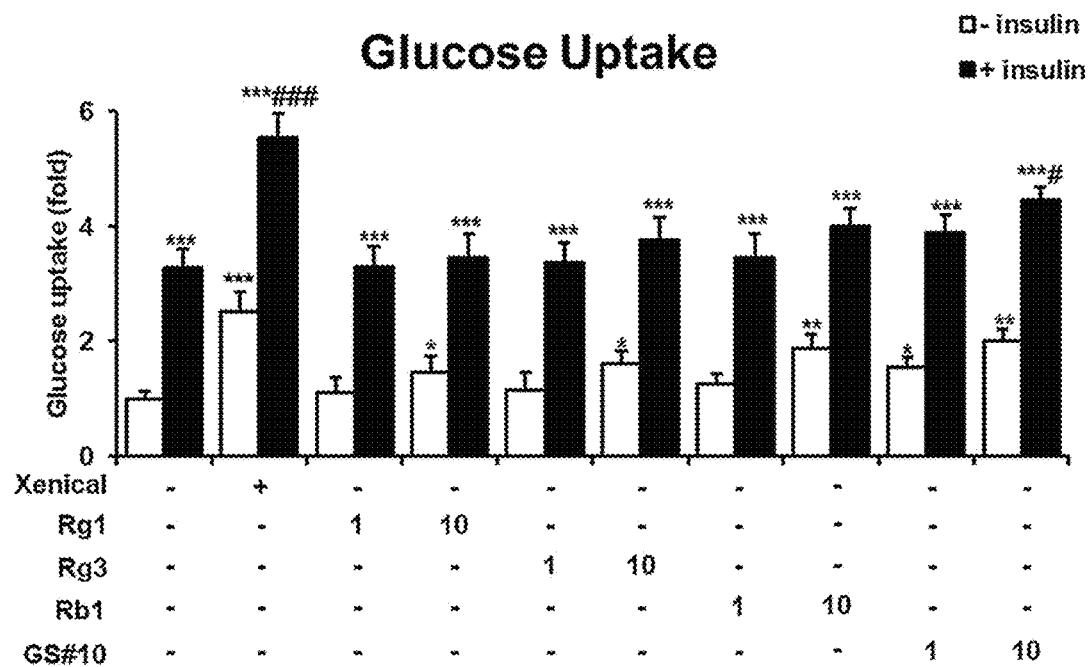
FIG. 16 is a diagram showing a comparison of the degree of glucose absorption promotion of ginsenosides Rg1, Rg3 and Rb1 of the red *Ginseng* index component and GS #10 corresponding to the novel ginsenoside of the present disclosure. (* $P<0.001$ vs. −insulin (−),  $P<0.01$ vs. −insulin (−), * $P<0.05$ vs. −insulin (−), ##$P<0.001$ vs. +insulin (−), #$P<0.51$ vs. +insulin (−))

As a result, as shown in FIGS. 14 to 16, the novel ginsenoside GS #10 of the present disclosure was found to have a much superior activity inhibitory effect of the polysaccharide digestive enzyme and glucose transport ability as compared with ginsenosides Rg1, Rg3, and Rb1, which are red *Ginseng* index components.

[Test Example 4] Cytotoxicity

The cell growth in the presence of novel ginsenoside GS #10, which is an example of the present disclosure, was evaluated using Cell Counting Kit (CCK)-8, in order to exclude the possibility that ginsenosides affect useful efficacy on the human body through cytotoxic activity. The experimental method is as follows.

10 µl of the CCK-8 reagent was added to the culturing SH-SY5Y cells (Dojindo, Md., USA) with reference to a 96-well plate, and left at 37° C. for 2 hours, and then the absorbance was measured at 450 nm. The cell viability was marked as a percentage (%) of the absolute optical density of each sample relative to the untreated sample. At this time, the concentration of the novel ginsenoside GS #10, which is an example of the present disclosure, contained in the medium in which the cells were cultured was 0.1, 1, 5, 10, 20, and 50 µM, respectively.

Figure 17:
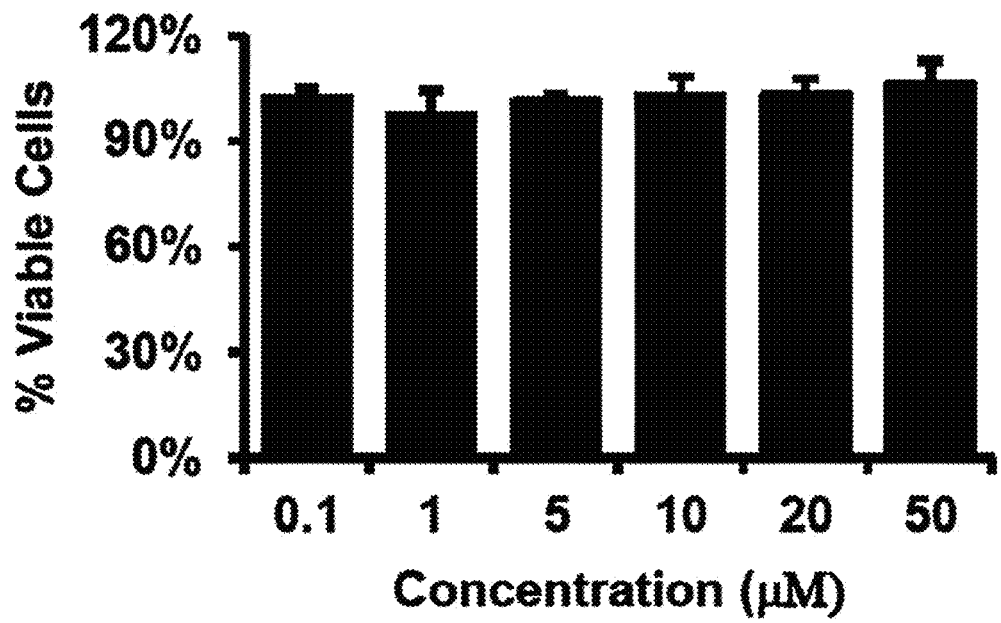
FIG. 17 is a diagram illustrating the cell viability (% Viable cells) of compound 10 (GS #10) corresponding to the novel ginsenoside of the present disclosure. (* $P<0.001$ vs. (−),  $P<0.01$ vs (−), * $P<0.05$ vs. (−))

As a result, as shown in FIG. 17, the novel ginsenoside GS #10, which is an example of the present disclosure, did not exhibit cytotoxicity up to 50 µM. These results indicate that the novel ginsenoside, which is an example of the present disclosure, may exhibit a useful effect on the human body without adversely affecting cell viability.

[Test Example 5] Comparison of Lipid Metabolism Inhibitory Effect 1

In order to compare the lipid metabolism inhibitory effect of the ginsenosides isolated from the *Ginseng* seed extract, the lipid synthesis-related gene expression inhibitory effect experiment was performed as follows.

The hepatocyte cell line HepG2 purchased from the International Center for Biological Resources (ATCC) were placed in Dulbecco's Modified Eagle's Medium (Sigma) to which 10% fetal bovine serum (Hyclone) and 1% penicillin/streptomycin (Sigma) were added, and cultured in a 5% $CO_2$ incubator. As a positive control, fenofibrate (FF, Sigma), which is used as an antihyperlipidemic drug, was used, and 7 kinds of ginsenosides (GS #01-GS #06, GS #10; 10 µM each) extracted from *Ginseng* seed were used for the experiment. After 24 hours of treatment, cells were collected, RNA was extracted using Trizol™ reagent (Thermo Fisher Scientific), and cDNA was synthesized using RevertAid™ 1st strand cDNA synthesis kit (Thermo Fisher Scientific). Bio-Rad's CFX96 real-time quantitative PCR (qPCR) instrument was used to observe the expression of the genes SREBP1c (sterol-regulatory element binding protein 1c), ACC (acetyl-CoA carboxylase) and FAS (Fatty acid synthase), which induces fat synthesis or accumulation. The results were shown in FIGS. 18 to 20.

Figure 18:
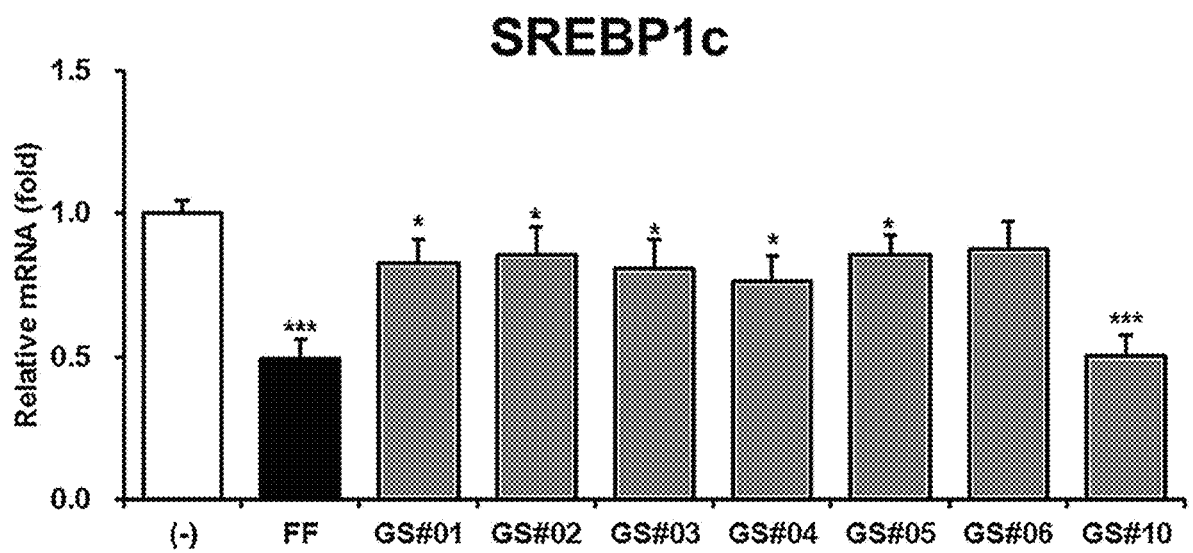
FIG. 18 is a diagram showing a comparison of the SREBP1c (sterol-regulatory element binding protein 1c) expression inhibitory ability of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* $P<0.001$ vs. (−),  $P<0.01$ vs. (−), * $P<0.05$ vs. (−))
Figure 19:
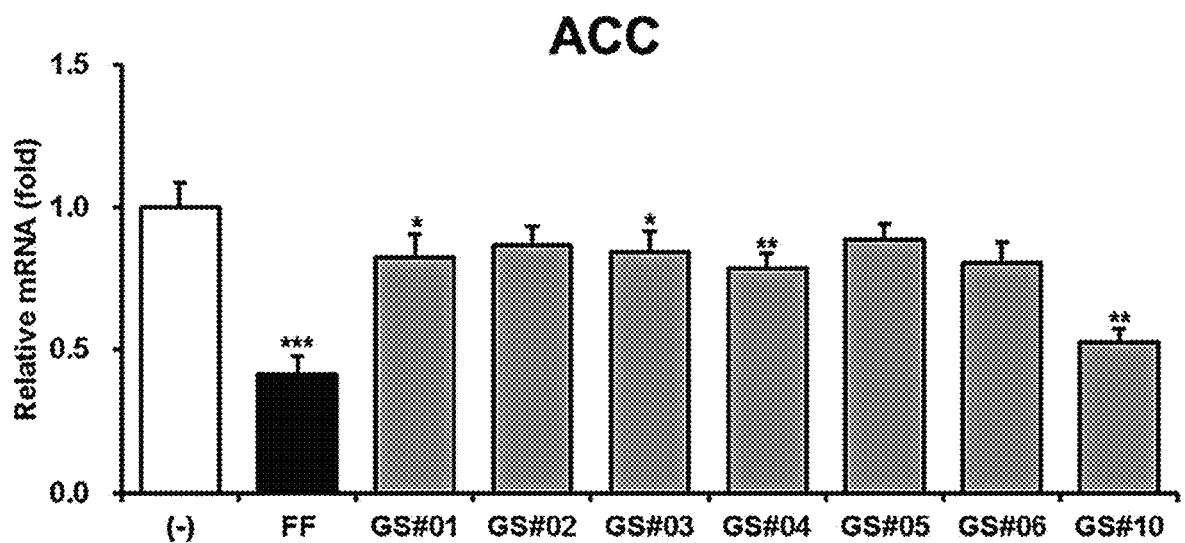
FIG. 19 is a diagram showing a comparison of the ACC (acetyl-CoA carboxylase) expression inhibitory ability of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* $P<0.001$ vs. (−),  $P<0.01$ vs. (−), * $P<0.05$ vs. (−))
Figure 20:
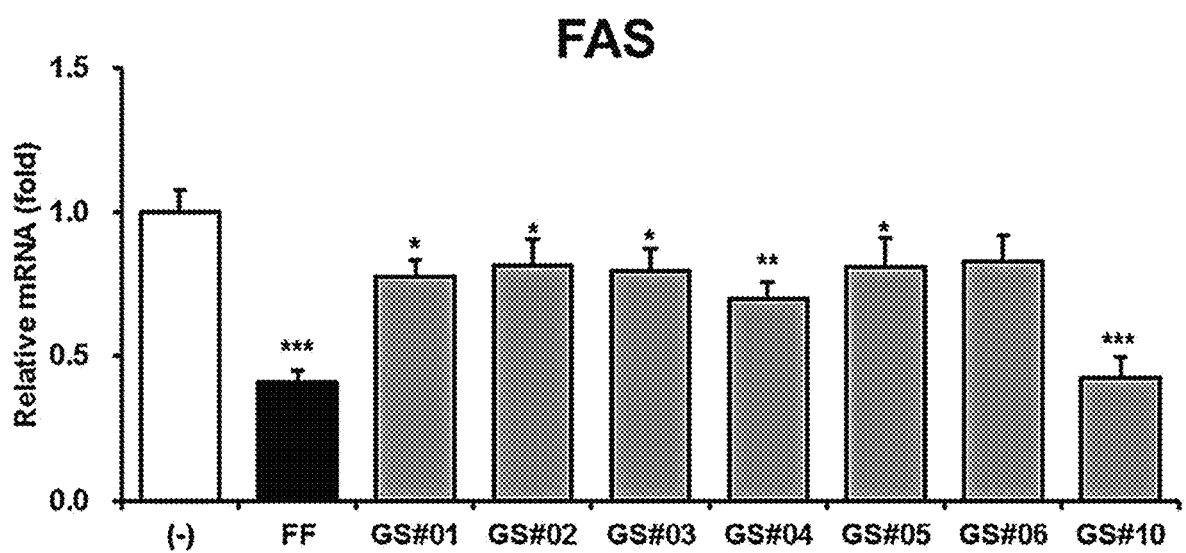
FIG. 20 is a diagram showing a comparison of the FAS (fatty acid synthase) expression inhibitory ability of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* $P<0.001$ vs. (−),  $P<0.01$ vs. (−), * $P<0.05$ vs. (−))

As shown in FIGS. 18 to 20, it was confirmed that the novel ginsenoside compound 10 (GS #10) of the present disclosure has a significantly higher expression inhibitory effect of the lipid synthesis-related genes at the same concentration than the previously known ginsenoside compounds 1-6 (GS #01-GS #06) as comparative examples of the present disclosure, and thus has excellent lipid synthesis or accumulation inhibitory effect in the body. This is due to the chemical structural difference. The novel ginsenoside $PG-RT_8$ of the present disclosure is far superior in efficacy of controlling or improving lipid metabolism among *Ginseng* seed-derived ginsenosides, and it means that it shows a stronger lipid metabolic control or improvement ability than the previously known steroidal saponin.

Figure 21:
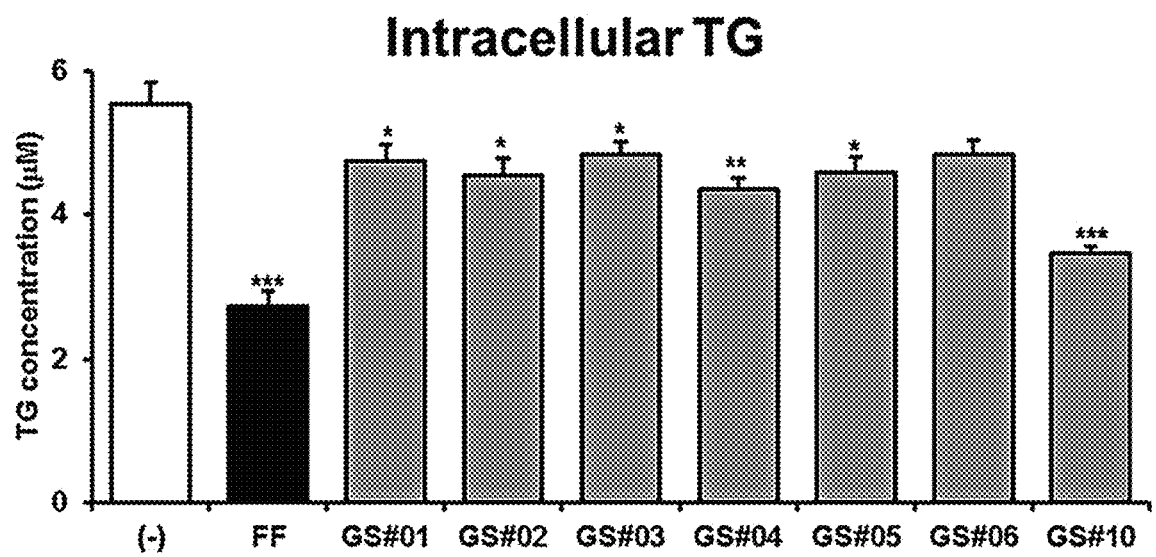
FIG. 21 is a diagram showing a comparison of the ability to inhibit lipid accumulation in hepatocytes of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* $P<0.001$ vs. (−),  $P<0.01$ vs. (−), * $P<0.05$ vs. (−))

In addition, in order to investigate whether inhibition of the expression of fat synthesis-related genes by ginsenoside derived from *Ginseng* seed may be involved in actual fat synthesis and accumulation, HepG2 cells were used to treat seven ginsenosides (GS #01-GS #06, GS #10; 10 µM each) and the control group (fenofibrate, FF) in the same manner as above, and then the Triglyceride Assay Kit (Abcam) was used to measure the amount of triglyceride (TG) accumulated in hepatocytes. The results were shown in FIG. 21. As a result, it was confirmed that the novel ginsenoside compound 10 (GS #10) of the present disclosure showed the most excellent inhibitory effect of lipid accumulation in hepatocytes.

[Test Example 6] Comparison of Lipid Metabolism Inhibitory Effect 2

Fats ingested through food are broken down and absorbed by the pancreatic lipase in the intestine. Accordingly, in order to reduce blood lipid concentration, lipid metabolism in the liver as well as lipolysis in the small intestine should be inhibited together. The following experiment was performed to investigate whether *Ginseng* seed-derived ginsenosides also affect fat digestion.

The hepatocyte cell line HepG2 purchased from the International Center for Biological Resources (ATCC) were placed in Dulbecco's Modified Eagle's Medium (Sigma) to which 10% fetal bovine serum (Hyclone) and 1% penicillin/streptomycin (Sigma) were added, and cultured in a 5% $CO_2$ incubator. As a positive control for the cells, Xenical (Sigma), which are used as pancreatic lipase inhibitors and anti-obesity therapeutic agents, and seven types of ginsenosides (GS #01-GS #06, GS #10; 10 µM each) extracted from *Ginseng* seed were treated for 1 hour. In addition, Pancreatic Lipase Activity Assay Kit (Abcam) was used to observe the inhibition of each lipase activity.

Figure 22:
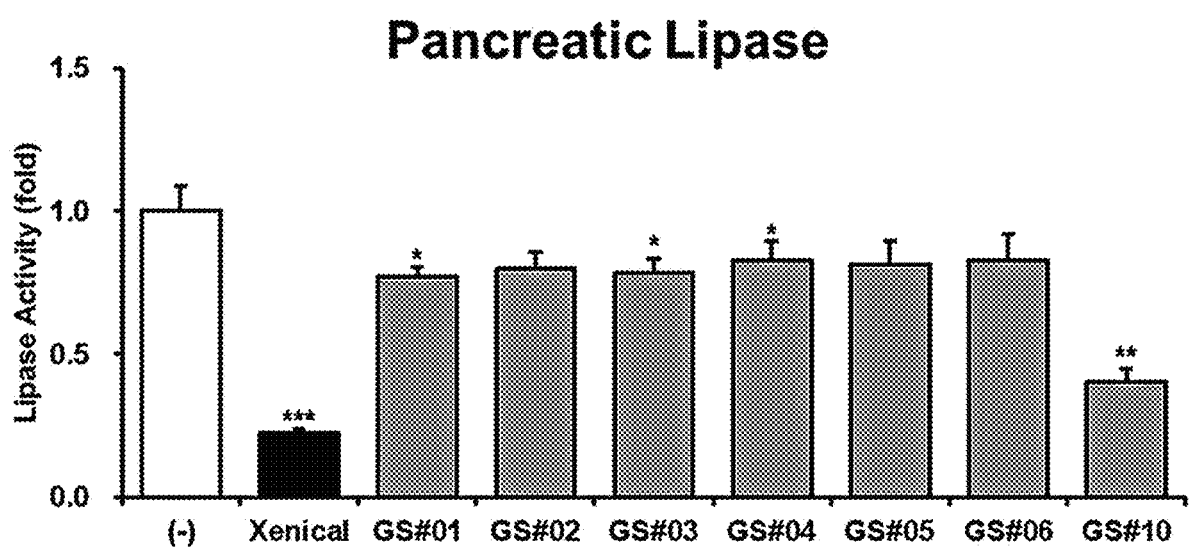
FIG. 22 is a diagram showing a comparison of the ability to inhibit pancreatic lipase activity of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* $P<0.001$ vs. (−),  $P<0.01$ vs. (−), * $P<0.05$ vs. (−))

As a result, as shown in FIG. 22, except for some of the previously known ginsenosides (GS #05, GS #06), all showed a significant inhibitory effect on pancreatic lipase activity. Among them, in particular, the lipase activity inhibitory effect of the novel ginsenoside compound 10 (GS #10) of the present disclosure was found to be the best, which was about 2 times or more than that of the conventional ginsenoside.

[Test Example 7] Comparison of Lipid Metabolism Inhibitory Effect 3

In order to compare the lipid metabolism inhibitory effect of the novel ginsenoside GS #10 (isolated from *Ginseng* seed extract), which is an embodiment of the present disclosure, with three types of ginsenosides (Rg1, Rg3, Rb1; Sigma), which are red *Ginseng* index components as a comparative example of the present disclosure, experiments were performed in the same manner as in Test Examples 5 and 6.

In this case, in order to observe the lipid synthesis-related gene expression and lipid accumulation inhibitory effect, HepG2 cells were treated with red *Ginseng* index components (Ginsenoside Rg1, Rg3, Rb1; Sigma) at 1 and 10 µM, respectively. Similarly, the novel ginsenoside compound 10 (GS #10) of the present disclosure was also treated at 1, 10 µM concentration for 24 hours.

Figure 23:
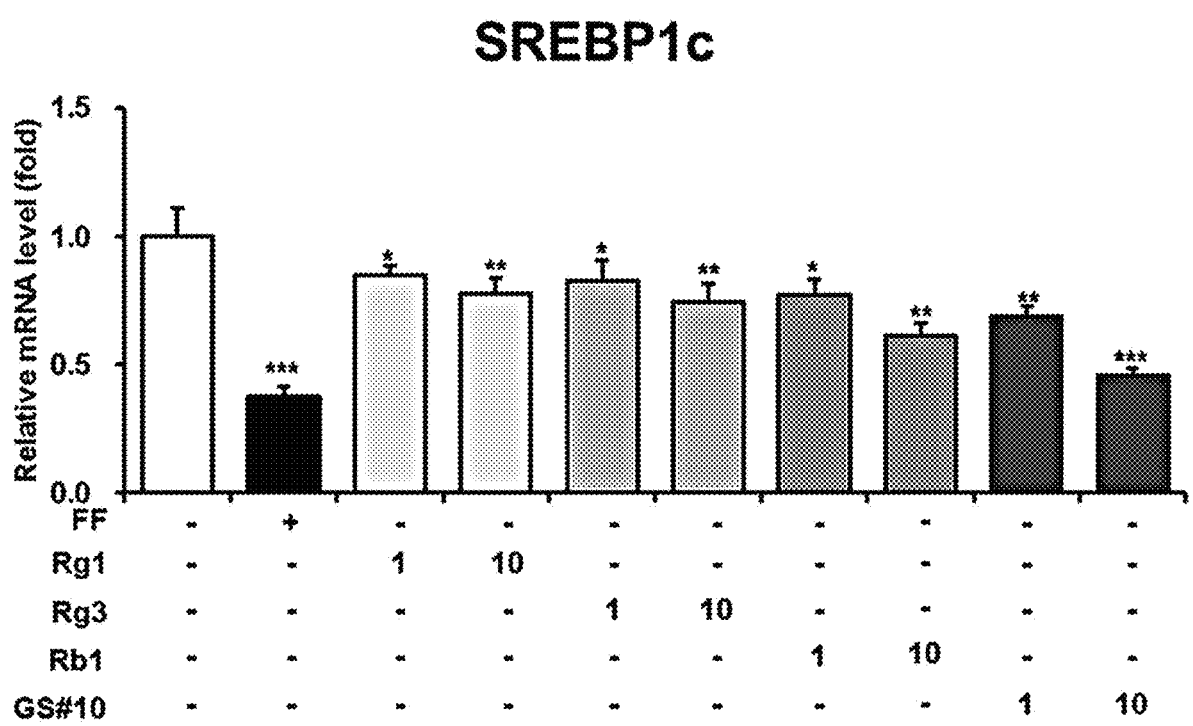
FIG. 23 is a diagram showing a comparison of the SREBP1c (sterol-regulatory element binding protein 1c) expression inhibitory ability of ginsenosides Rg1, Rg3 and Rb1 of the red *Ginseng* index component and compound 10 (GS #10) corresponding to the novel ginsenoside of the present disclosure, by concentration (1 μM, 10 μM). (* $P<0.001$ vs. (−),  $P<0.01$ vs. (−), * $P<0.05$ vs. (−))
Figure 24:
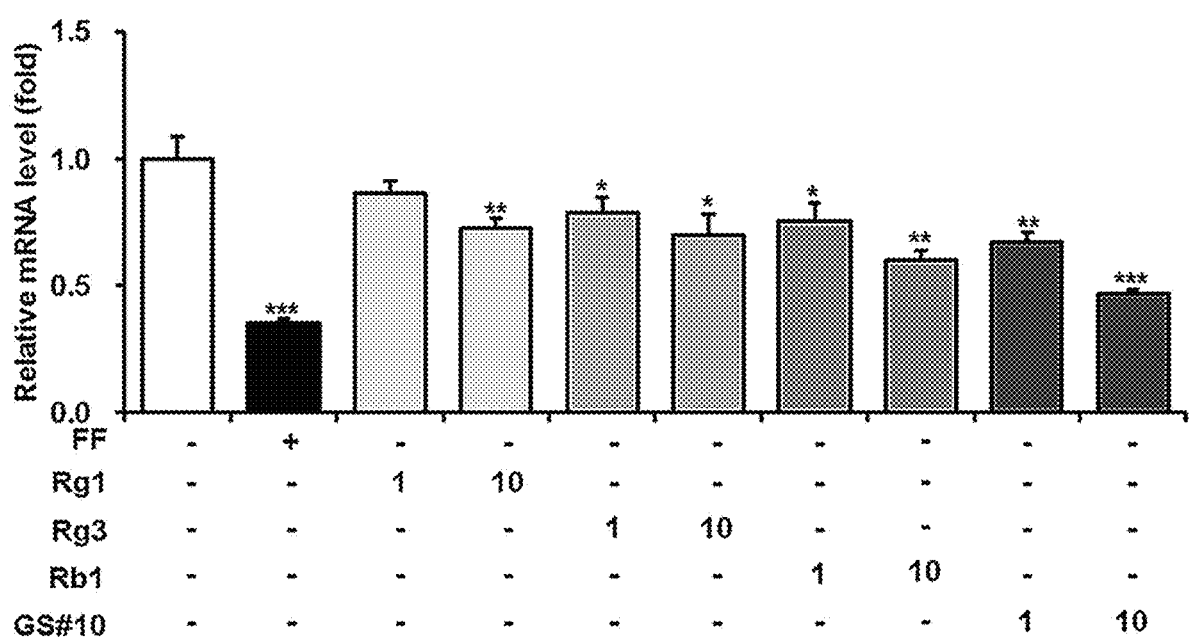
FIG. 24 is a diagram showing a comparison of the ACC (acetyl-CoA carboxylase) expression inhibitory ability of ginsenosides Rg1, Rg3 and Rb1 of the red *Ginseng* index component and compound 10 (GS #10) corresponding to the novel ginsenoside of the present disclosure, by concentration (1 μM, 10 μM). (* $P<0.001$ vs. (−),  $P<0.01$ vs. (−), * $P<0.05$ vs. (−))
Figure 25:
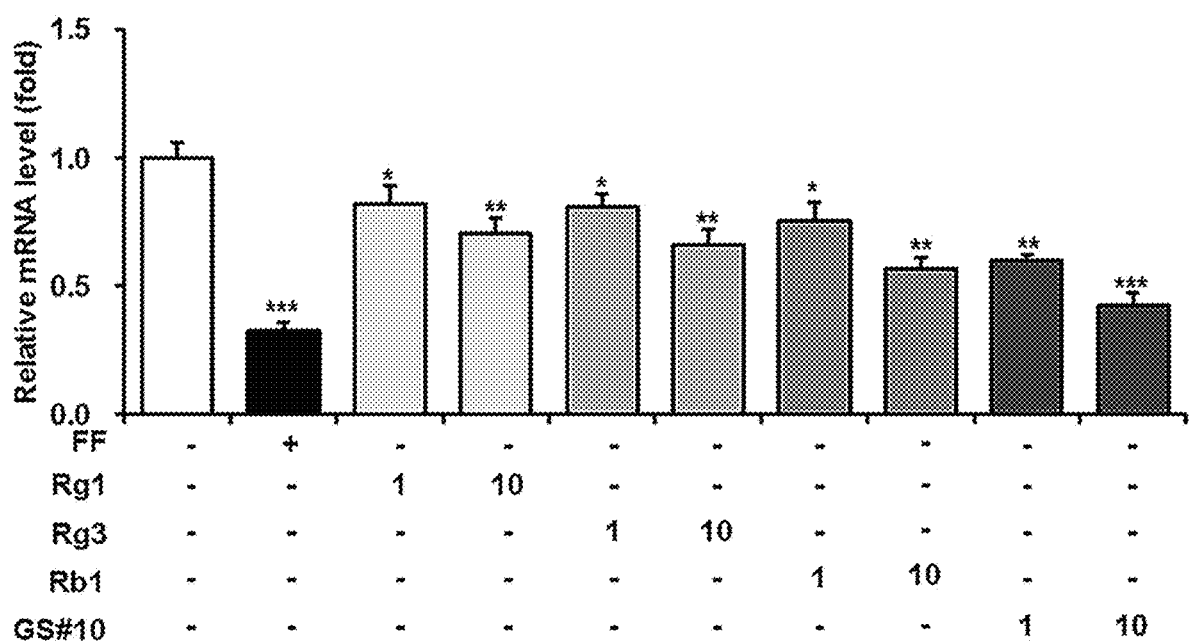
FIG. 25 is a diagram showing a comparison of the FAS (fatty acid synthase) expression inhibitory ability of ginsenosides Rg1, Rg3 and Rb1 of the red *Ginseng* index component and compound 10 (GS #10) corresponding to the novel ginsenoside of the present disclosure, by concentration (1 μM, 10 μM). (* $P<0.001$ vs. (−),  $P<0.01$ vs. (−), * $P<0.05$ vs. (−))
Figure 26:
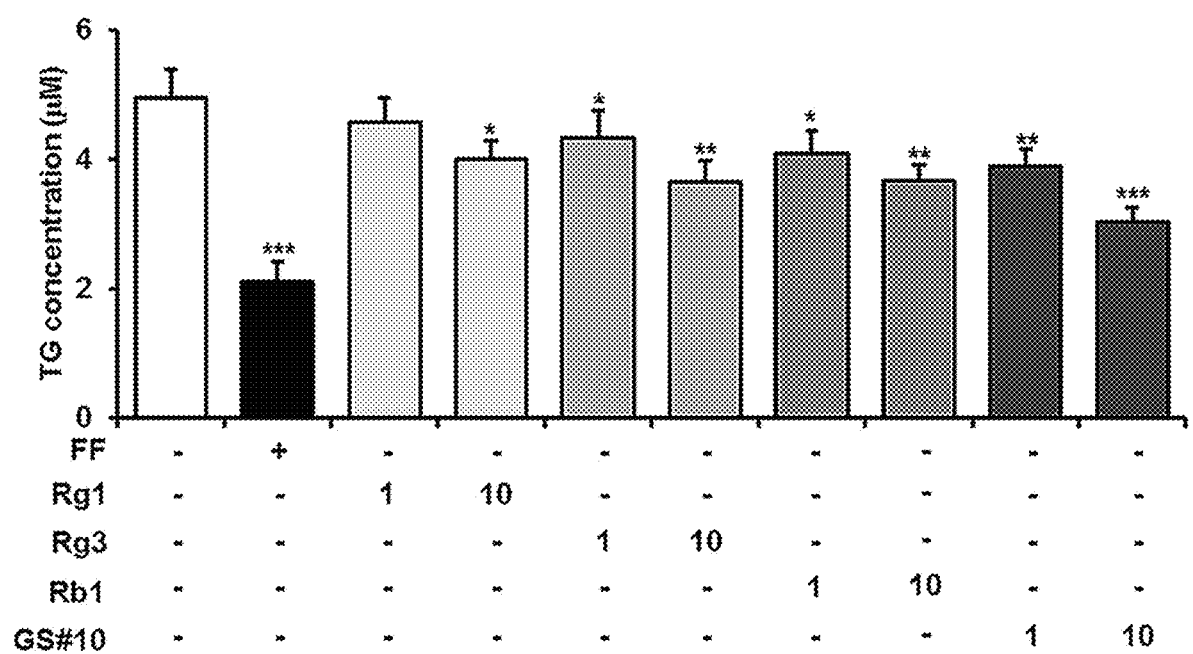
FIG. 26 is a diagram showing a comparison of the ability to inhibit lipid accumulation in hepatocytes of ginsenosides Rg1, Rg3 and Rb1 of the red *Ginseng* index component and compound 10 (GS #10) corresponding to the novel ginsenoside of the present disclosure, by concentration (1 μM, 10 μM). (* P<0.001 vs. (-),  P<0.01 vs. (-), * P<0.05 vs. (-))
Figure 27:
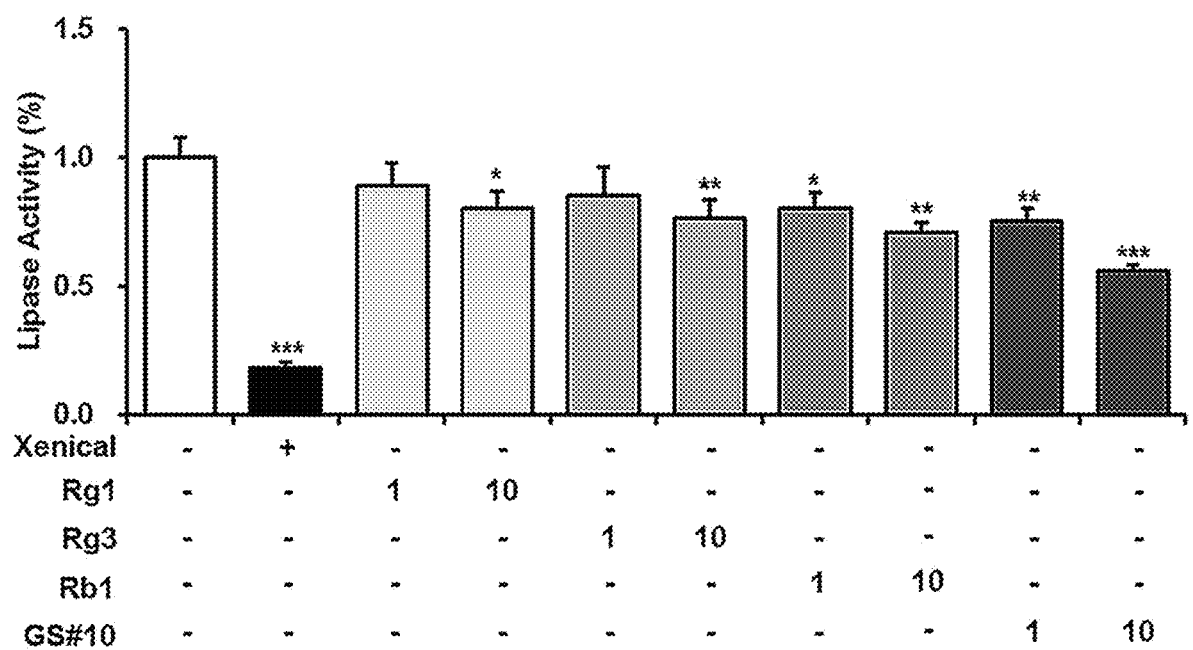
FIG. 27 is a diagram showing a comparison of the ability to inhibit pancreatic lipase activity of ginsenosides Rg1, Rg3 and Rb1 of the red *Ginseng* index component and compound 10 (GS #10) corresponding to the novel ginsenoside of the present disclosure, by concentration (1 μM, 10 μM). (* P<0.001 vs. (-),  P<0.01 vs. (-), * P<0.05 vs. (-))

The expression of lipid synthesis-related genes is shown in FIGS. 23 to 25, and the amount of triglyceride accumulated in hepatocytes is shown in FIG. 26. Finally, the activity of pancreatic lipase was measured and shown in FIG. 27. As shown in FIGS. 23 to 27, it was confirmed that the novel ginsenoside GS #10 of an embodiment of the present disclosure is far superior in lipid metabolism inhibitory effect to three types of ginsenosides that constitute red Ginseng index components.

[Test Example 8] Comparison of Efficacy in Controlling Gene Activity Related to Cholesterol Synthesis 1

In order to compare the efficacy in controlling the gene activity related to cholesterol synthesis of ginsenosides isolated from the Ginseng seed extract, the following experiments were performed.

The hepatocyte cell line HepG2 purchased from the International Center for Biological Resources (ATCC) were placed in Dulbecco's Modified Eagle's Medium (Sigma) to which 10% fetal bovine serum (Hyclone) and 1% penicillin/streptomycin (Sigma) were added, and cultured in a 5% $CO_2$ incubator. As a positive control, Simvastatin (Sigma Aldrich; St. Louis, Mo.), which is known as a lipid lowering agent of the HMG-CoA reductase inhibitor family and reduces cholesterol production in the blood, was used. For the experiment, seven types of ginsenoside (GS #01-GS #06, GS #10; 10 µM each) extracted from Ginseng seeds were treated for 24 hours, and the cells were collected. RNA was extracted using Trizol™ reagent (Thermo Fisher Scientific) and cDNA was synthesized using RevertAid™ 1st strand cDNA synthesis kit (Thermo Fisher Scientific). Bio-Rad's CFX96 real-time quantitative PCR (qPCR) instrument was used to observe the expression of HMG-CoA (3-hydroxy-3-methyl-glutaryl-coenzyme A) reductase, a key gene for cholesterol synthesis. The results were shown in FIG. 28. In the same way, LDL (low-density lipoprotein) was absorbed into cells, and the expression of LDL receptor (LDLR), which serves to lower blood cholesterol levels, was observed. The results were shown in FIG. 29.

Figure 28:
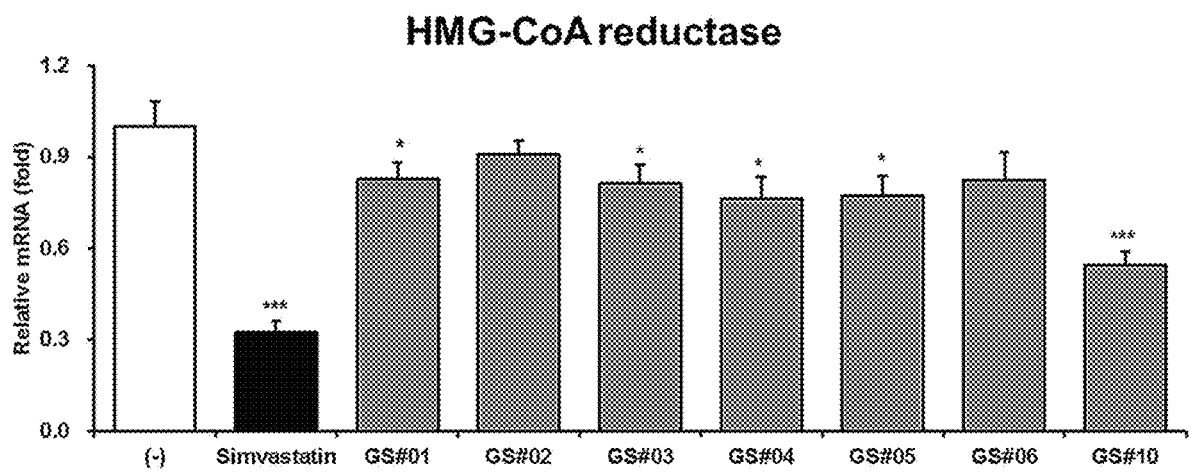
FIG. 28 is a diagram showing a comparison of the expression levels of HMG-CoA (3-hydroxy-3-methyl-glutaryl-coenzyme A reductase), a key gene for cholesterol synthesis, of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (*** P<0.001 vs. (-), * P<0.05 vs. (-))
Figure 29:
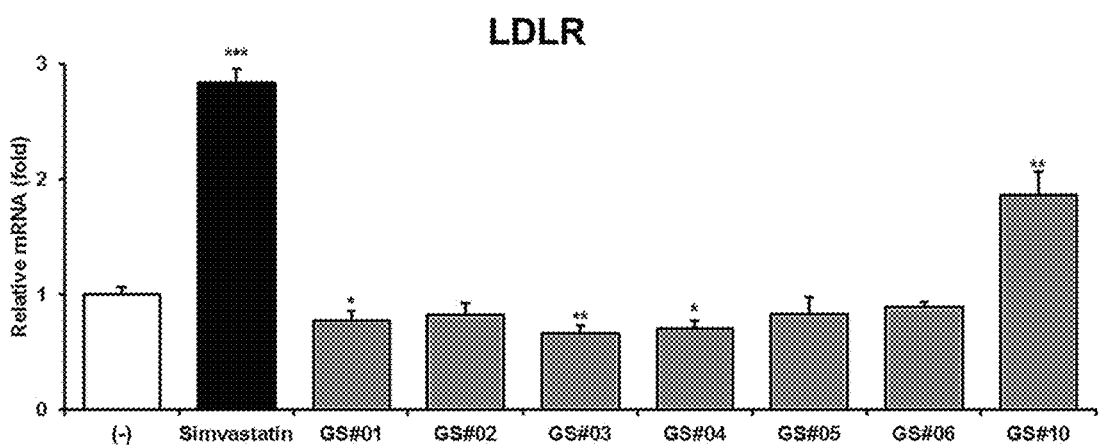
FIG. 29 is a diagram showing a comparison of the expression levels of LDL receptor (LDLR), which plays a role in lowering blood cholesterol level, of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* P<0.001 vs. (-),  P<0.01 vs. (-), * P<0.05 vs. (-))

As a result, all seven types of Ginseng seed-derived ginsenosides were found to reduce the expression of HMG-CoA reductase, and among them, the novel ginsenoside GS #10 of the present disclosure had the most excellent efficacy of inhibiting the expression (FIG. 28). In the case of LDL receptor (LDLR), ginsenoside GS #1 to 6 previously known among seven types of ginsenosides derived from Ginseng seed did not show a significant change in expression level, whereas the novel ginsenoside GS #10 of an embodiment of the present disclosure increased the expression level more than about 2 times compared to the control (−) (FIG. 29).

Figure 30:
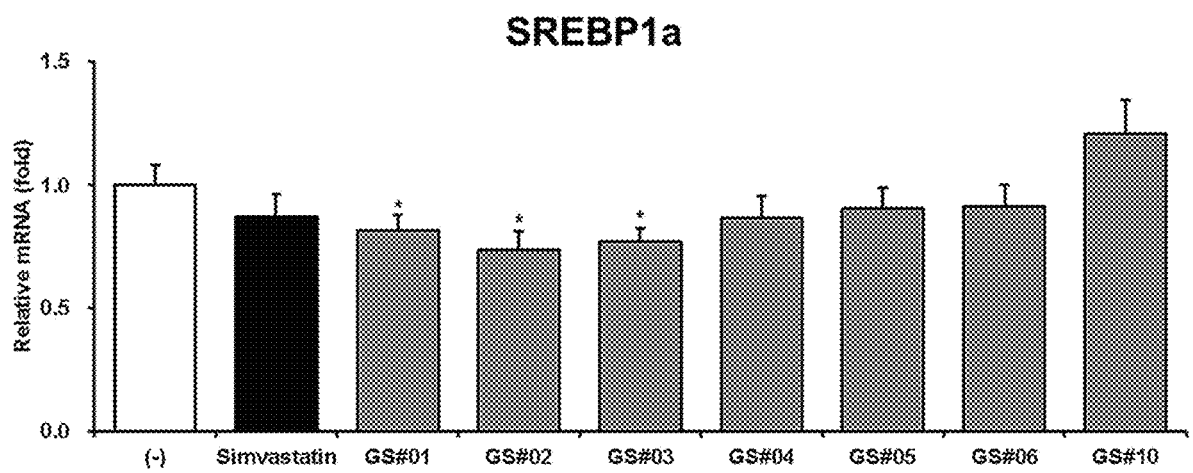
FIG. 30 is a diagram showing a comparison of the expression levels of SREBP1a, which is involved in cholesterol metabolism, of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* P<0.05 vs. (-))

LDLR is controlled by the SREBP1a gene. SREBP1c of Test Example 1 is involved in glucose metabolism and fatty acid synthesis, while SREBP1a, a transcription factor of the same family as SREBP1c, is involved in cholesterol metabolism. In this experiment, the expression of SREBP1a involved in cholesterol metabolism of seven types of ginsenosides derived from Ginseng seeds was observed. As a result, ginsenosides GS #1 to 6 previously known among seven types of ginsenosides derived from Ginseng seeds also inhibit the expression of SREBP1a as well as SREBP1c, whereas the novel ginsenoside GS #10 of an embodiment of the present disclosure did not inhibit the expression of SREBP1a but rather tended to increase the expression thereof (FIG. 30). This result is also different from the positive control. The results show that only novel ginsenoside GS #10 of an embodiment of the present disclosure can effectively reduce blood cholesterol levels through a dual mechanism of action through inhibition of cholesterol synthesis and promotion of cholesterol intracellular absorption.

[Test Example 9] Comparison of Efficacy in Controlling Gene Activity Related to Cholesterol Synthesis 2

In order to compare the efficacy in controlling the gene activity related to cholesterol synthesis of the novel ginsenoside GS #10 of an embodiment of the present disclosure with the three types of ginsenosides (Rg1, Rg3, Rb1; Sigma) which are red Ginseng index components, the experiment was performed in the same manner as in Test Example 8. At this time, HepG2 cells were treated with red Ginseng index components (Ginsenoside Rg1, Rg3, Rb1; Sigma) and the novel ginsenoside GS #10 at concentrations of 1 and 10 µM each for 24 hours.

Figure 31:
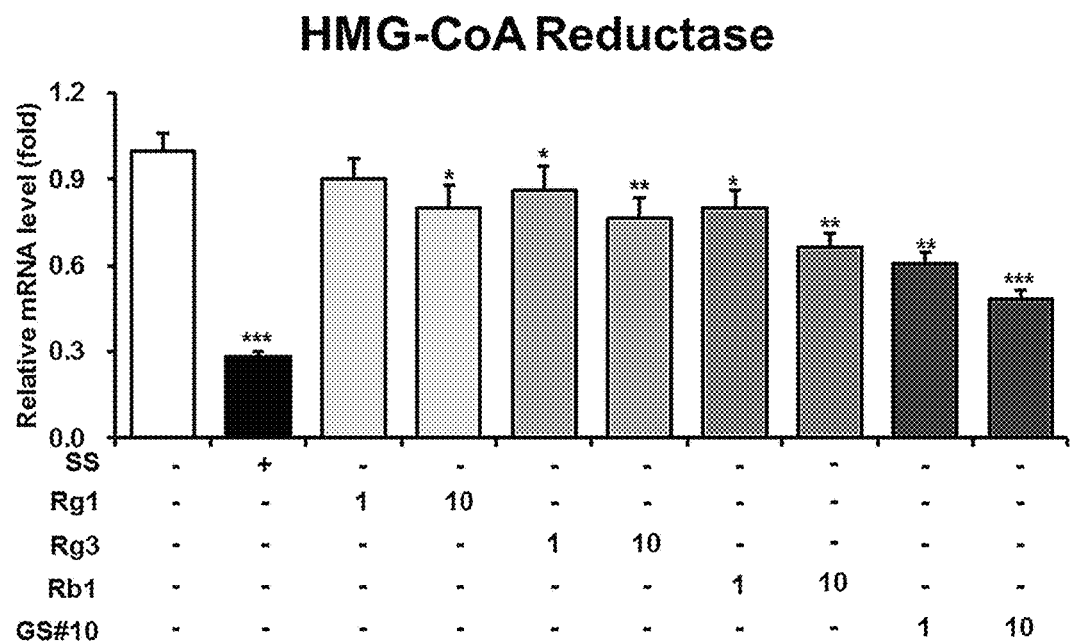
FIG. 31 is a diagram showing a comparison of the expression levels of HMG-CoA (3-hydroxy-3-methyl-glutaryl-coenzyme A reductase), which is a key gene for cholesterol synthesis, of ginsenosides Rg1, Rg3 and Rb1 of the red *Ginseng* index component and compound 10 (GS #10) corresponding to the novel ginsenoside of the present disclosure. (*** P<0.001 vs. (-),* P<0.05 vs. (-))
Figure 32:
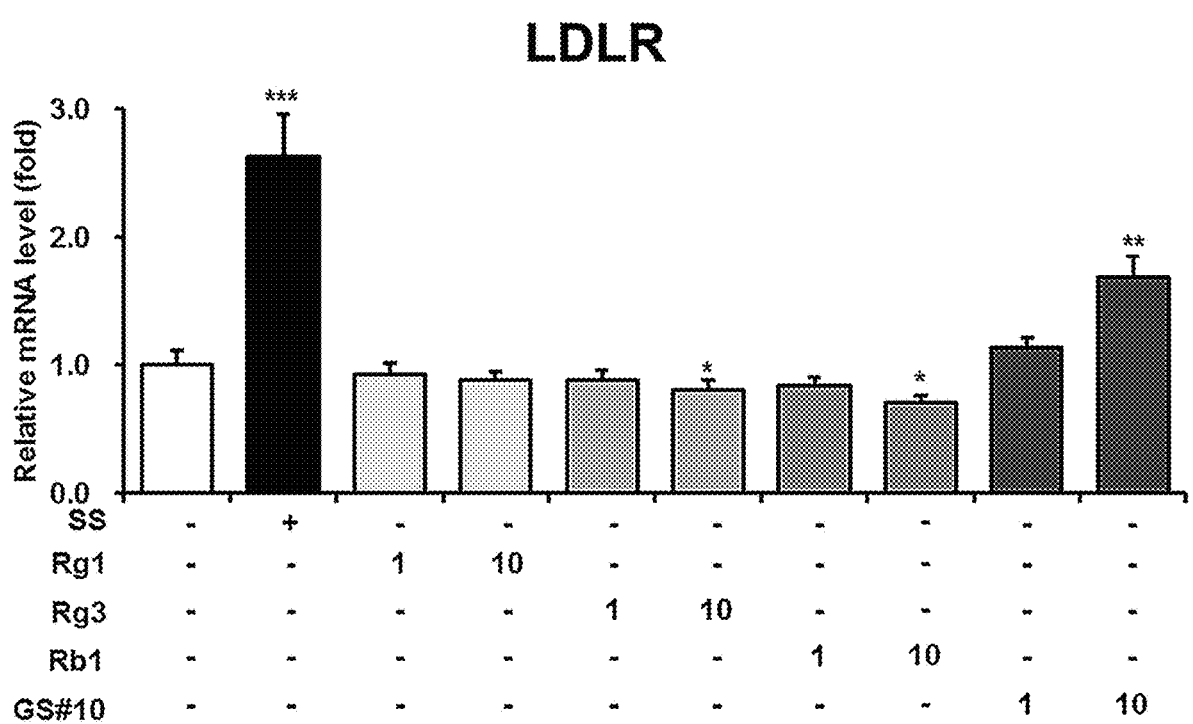
FIG. 32 is a diagram showing a comparison of the expression levels of LDL receptor (LDLR), which plays a role in lowering blood cholesterol level, of ginsenosides Rg1, Rg3 and Rb1 of the red *Ginseng* index component and compound 10 (GS #10) corresponding to the novel ginsenoside of the present disclosure. (* P<0.001 vs. (-),  P<0.01 vs. (-), * P<0.05 vs. (-))
Figure 33:
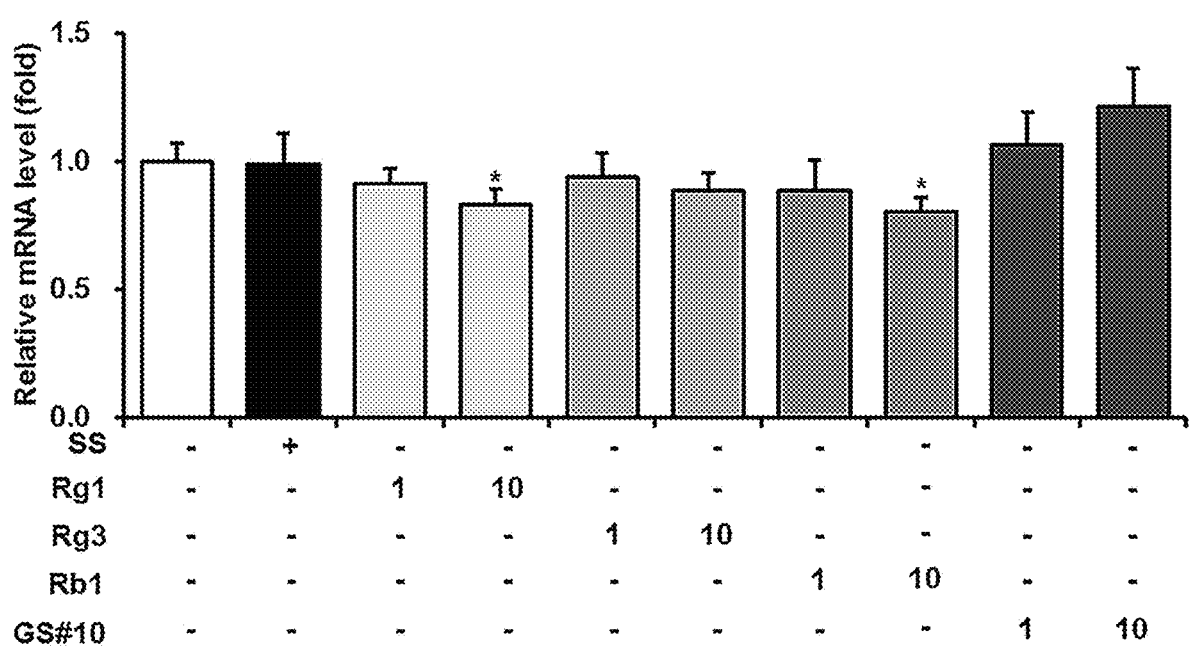
FIG. 33 is a diagram showing a comparison of the expression levels of SREBP1a, which is involved in cholesterol metabolism, of ginsenosides Rg1, Rg3 and Rb1 of the red *Ginseng* index component and compound 10 (GS #10) corresponding to the novel ginsenoside of the present disclosure. (* P<0.05 vs. (-))

As a result, as shown in FIGS. 31 to 33, the novel ginsenoside GS #10 of an embodiment of the present disclosure was most effective in inhibiting cholesterol synthesis and promoting intracellular transport. This means that the novel ginsenoside GS #10 of an embodiment of the present disclosure will have better cholesterol metabolism controlling efficacy than three types of red Ginseng index ginsenosides.

[Test Example 10] Comparison of Adipocyte Differentiation Inhibitory Effect 1

In order to compare the anti-obesity effect of ginsenosides isolated from the Ginseng seed extract, an adipocyte differentiation inhibitory effect experiment was performed as follows.

The adipocyte cell 3T3-L1 purchased from the International Center for Biological Resources (ATCC) were placed in Dulbecco's Modified Eagle's Medium (Sigma) to which 10% fetal bovine serum (Hyclone) and 1% penicillin/streptomycin (Sigma) were added, and cultured in a 5% $CO_2$ incubator. In order to differentiate preadipocytes into adipocytes, the cells were filled in a culture plate and cultured. After 48 hours, the cells were replaced with Dulbecco's modified eagle medium (DMEM) to which 10% of fetal bovine serum (Hyclone), 0.5 mM of 3-isobutyl-1-methyl-xanthine (Sigma), 1 µM of dexamethasone (Sigma), 5 µg/ml of insulin (Sigma), 1% of penicillin/streptomycin (Sigma) were added and further cultured for 48 hours. During 48 hours of culture, seven types of ginsenoside reagents (GS #01-GS #06, GS #10) extracted from Ginseng seeds were treated at 10 µM each to affect adipocyte differentiation. As a control to confirm the effect of inhibiting adipocyte differentiation, 20 µM of bisphenol A diglycidyl ether (BADGE) (Sigma), a PPARγ (Peroxisome proliferator-activated receptor gamma) antagonist, was used. Thereafter, the cells were further cultured for 10 days while being replaced with a medium containing 10% FBS and 5 µg/ml insulin and 1% penicillin/streptomycin at two-day intervals to induce adipocyte differentiation.

Figure 34:
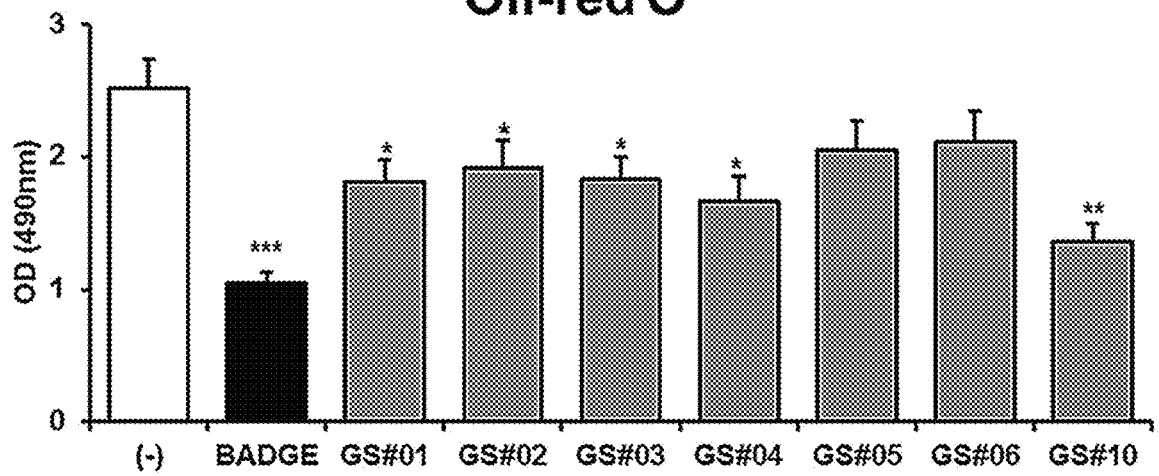
FIG. 34 is a diagram showing a comparison of the ability to inhibit fat accumulation in adipocytes of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* P<0.001 vs. (-),  P<0.01 vs (-), * P<0.05 vs. (-))

Differentiated adipocytes treated with each of the seven types of ginsenosides were fixed with formaldehyde solution (Sigma), stained with Oil-red O staining solution (Sigma), and then dissolved with isopropanol (Sigma), and then the amount of the stained fat was quantified by measuring at 490 nm absorbance. The quantitative results were shown in FIG. 34. As shown in FIG. 34, except some (GS #05, GS #06) of seven types of ginsenosides (GS #01-GS #06, GS #10; 10 μM each) extracted from *Ginseng* seeds, all of them was observed to reduce the amount of fats in adipocytes. Among them, the novel ginsenoside compound 10 (GS #10) of the present disclosure was found to have the most excellent fat accumulation inhibitory effect.

Figure 35:
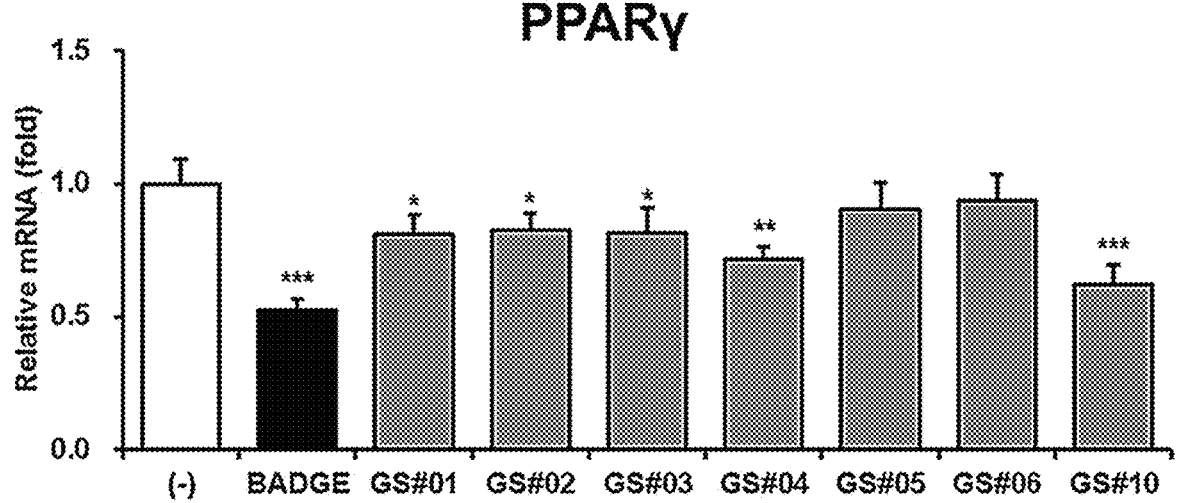
FIG. 35 is a diagram showing a comparison of the ability to inhibit PPARγ gene expression of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* P<0.001 vs. (-),  P<0.01 vs (-), * P<0.05 vs. (-))
Figure 36:
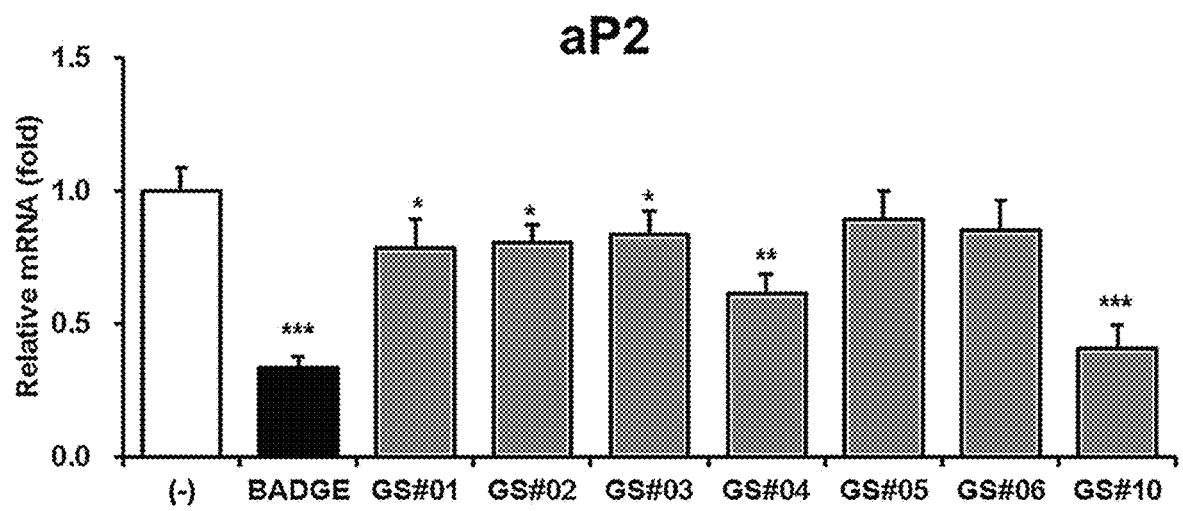
FIG. 36 is a diagram showing a comparison of the ability to inhibit aP2 gene expression of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* P<0.001 vs. (-),  P<0.01 vs (-), * P<0.05 vs. (-))
Figure 37:
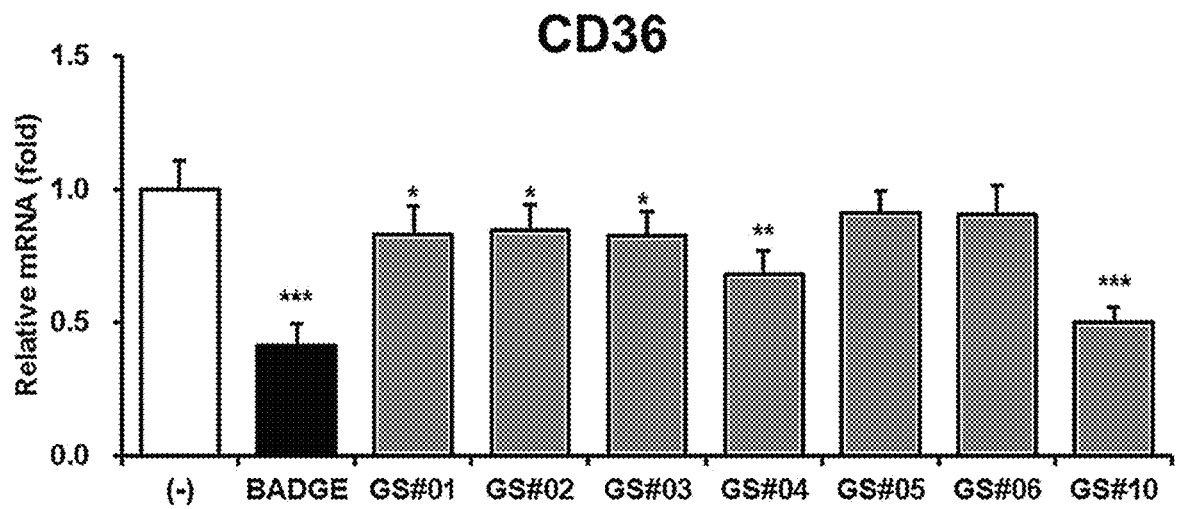
FIG. 37 is a diagram showing a comparison of the ability to inhibit CD36 gene expression of compounds 1 to 6 (GS #01-GS #06) corresponding to the previously known ginsenosides among the compounds fractionated from *Ginseng* seed extract and compound 10 (GS #10) corresponding to the novel ginsenoside of the present disclosure. (* P<0.001 vs. (-),  P<0.01 vs (-), * P<0.05 vs. (-))

After the differentiation of adipocytes in the same manner as above, the expressions of PPARγ (Peroxisome proliferator-activated receptor gamma), aP2 (Adipocyte protein 2) and CD36 were observed as adipocyte marker genes. RNA was extracted using Trizol™ reagent (Thermo Fisher Scientific), and cDNA was synthesized using RevertAid™ 1st strand cDNA synthesis kit (Thermo Fisher Scientific). Bio-Rad's CFX96 real-time quantitative PCR (qPCR) instrument was used to quantify the expression levels of each gene. The results were shown in FIGS. 35 to 37. As in the results in FIG. 34, the effect of inhibiting the adipocyte differentiation of the previously known ginsenosides GS #01 to GS #04 and the novel ginsenoside compound 10 (GS #10) of the present disclosure was observed. It can be seen that the novel ginsenoside compound 10 (GS #10) of the present disclosure is more effective in inhibiting the adipocyte differentiation than *Ginseng* seed-derived ginsenosides.

[Test Example 11] Comparison of Adipocyte Differentiation Inhibitory Effect 2

The adipocyte differentiation inhibitory effect was compared in the same manner as in Test Example 10, and the novel ginsenoside GS #10 (isolated from *Ginseng* seed extract) of an embodiment of the present disclosure was compared with three types of ginsenosides (Rg1, Rg3, Rb1; Sigma) which are red *Ginseng* index components as a comparative example of the present disclosure. At this time, the concentration of each ginsenoside was 1 μM and 10 μM.

Figure 38:
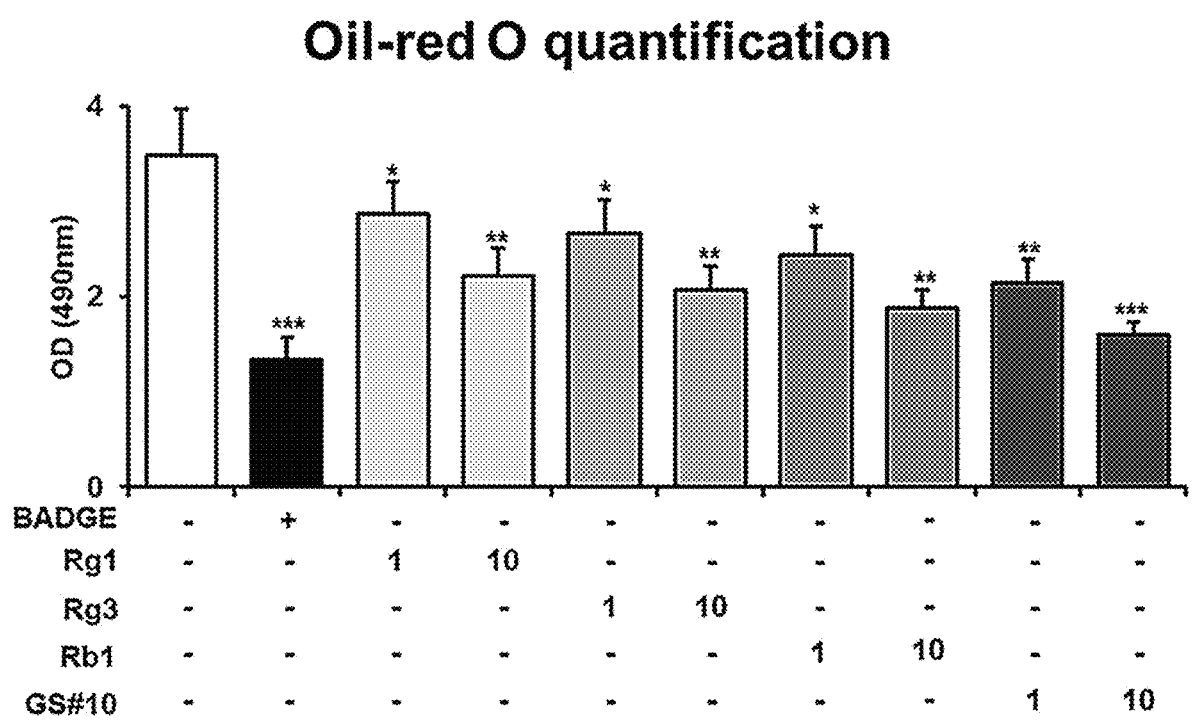
FIG. 38 is a diagram showing a comparison of the ability to inhibit fat accumulation in adipocytes of ginsenosides Rg1, Rg3 and Rb1 of the red *Ginseng* index component and compound 10 (GS #10) corresponding to the novel ginsenoside of the present disclosure, by concentration (1 μM, 10 μM). (* P<0.001 vs. (-),  P<0.01 vs (-), * P<0.05 vs. (-))
Figure 39:
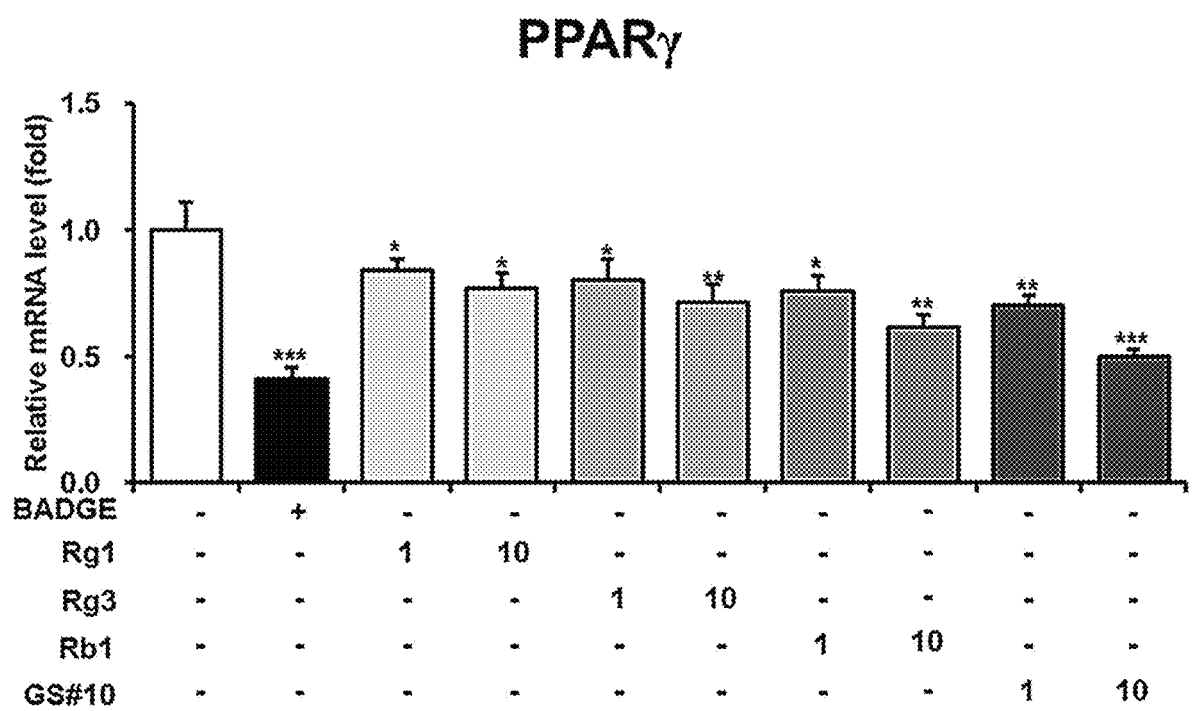
FIG. 39 is a diagram showing a comparison of the ability to inhibit PPARγ gene expression of ginsenosides Rg1, Rg3 and Rb1 of the red *Ginseng* index component and compound 10 (GS #10) corresponding to the novel ginsenoside of the present disclosure, by concentration (1 μM, 10 μM). (* P<0.001 vs. (-),  P<0.01 vs (-), * P<0.05 vs. (-))
Figure 40:
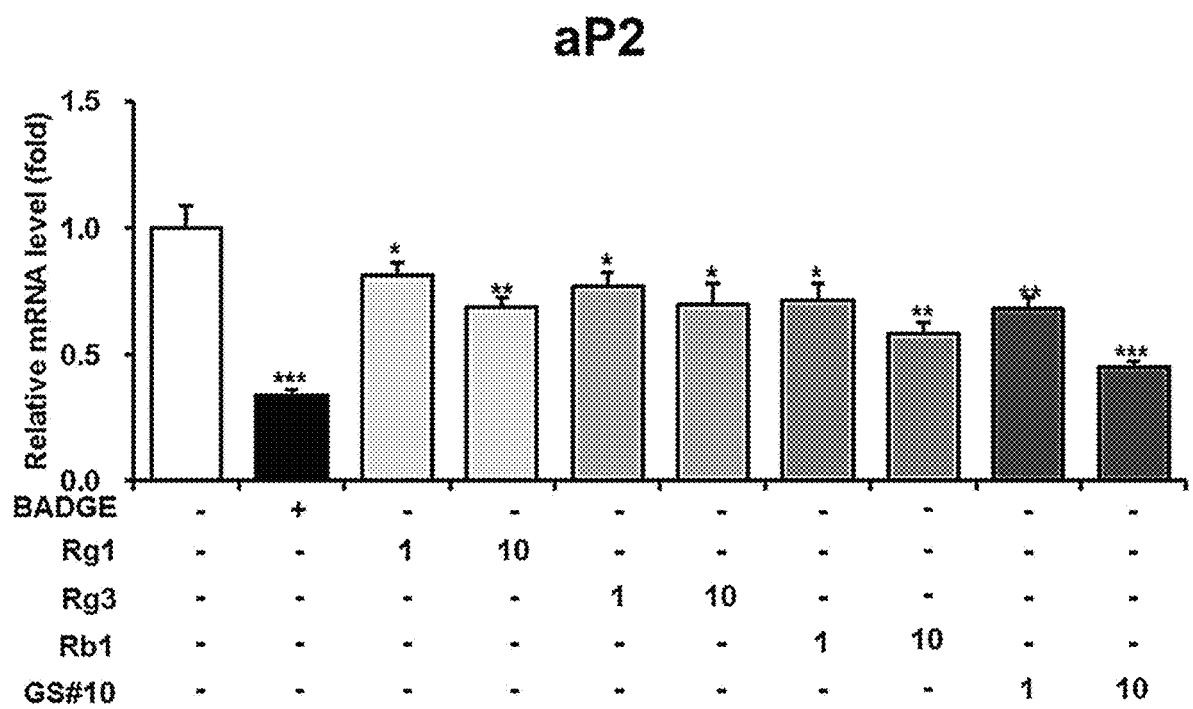
FIG. 40 is a diagram showing a comparison of the ability to inhibit aP2 gene expression of ginsenosides Rg1, Rg3 and Rb1 of the red *Ginseng* index component and compound 10 (GS #10) corresponding to the novel ginsenoside of the present disclosure, by concentration (1 μM, 10 μM). (* P<0.001 vs. (-),  P<0.01 vs (-), * P<0.05 vs. (-))
Figure 41:
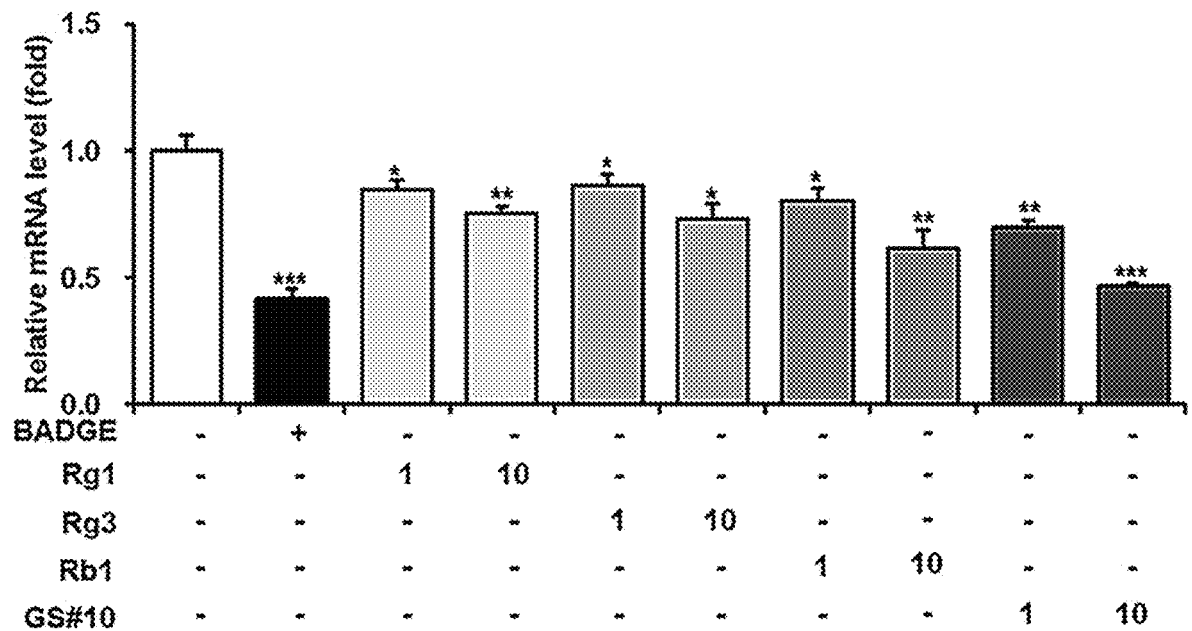
FIG. 41 is a diagram showing a comparison of the ability to inhibit CD36 gene expression of ginsenosides Rg1, Rg3 and Rb1 of the red *Ginseng* index component and compound 10 (GS #10) corresponding to the novel ginsenoside of the present disclosure, by concentration (1 μM, 10 μM). (* P<0.001 vs. (-),  P<0.01 vs (-), * P<0.05 vs. (-))

The amount of triglyceride accumulated in adipocytes was shown in FIG. 38, and the expression of adipocyte marker genes was shown in FIGS. 39 to 41. It was confirmed that when compared to ginsenosides Rg1, Rg3, Rb1 of the red *Ginseng* index components, the novel ginsenoside GS #10 of the example of the present disclosure is far superior in adipocyte differentiation inhibition and fat accumulation inhibitory effect.

[Test Example 12] Comparison of Blood Flow Increase Effect

The nitric oxide (NO) produced by vascular endothelial cells expands blood vessels and increases blood flow, and thus if nitric oxide production in vascular endothelial cells can be increased, it means that blood circulation can also be improved by increasing blood flow.

Figure 42:
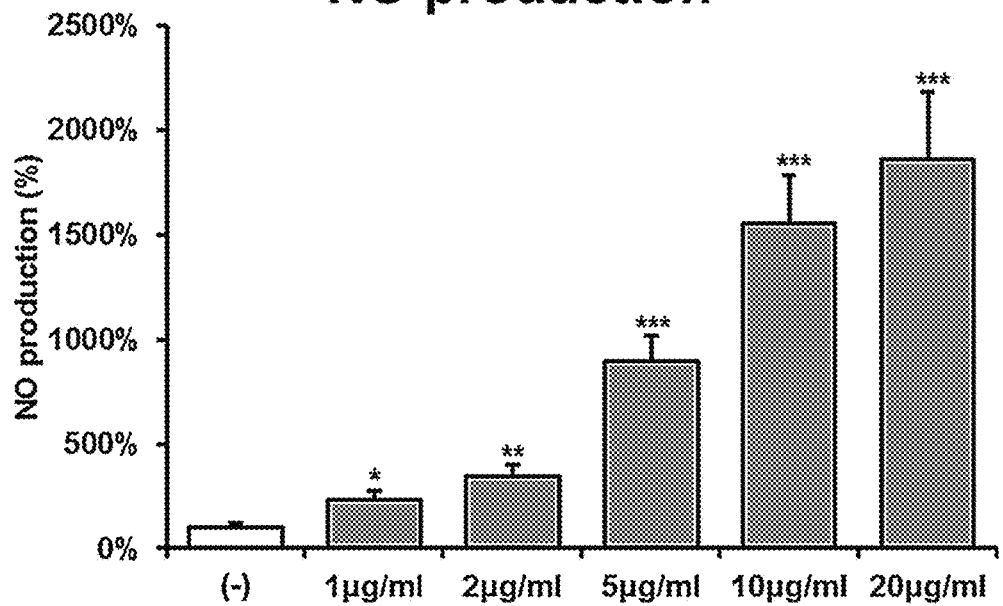
FIG. 42 is a diagram showing a measurement of the production amount of nitric oxide (NO) according to the concentration of GS #10 corresponding to the novel ginsenoside of the present disclosure isolated from *Ginseng* seed extract. (* P<0.001 vs. (-),  P<0.01 vs. (-), * P<0.05 vs. (-))

Since nitric oxide is made by epithelial nitric oxide synthase (eNOS), in this experiment, it was confirmed whether the novel ginsenoside GS #10 of the example of the present disclosure can promote the production of nitric oxide through eNOS activity control in vascular endothelial cells. Specifically, the human umbilical vein endothelial cells (HUVEC) were purchased from the International Center for Biological Resources (ATCC) and cultured, and then the amount of nitric oxide (NO) produced by treating the novel ginsenoside GS #10 at a concentration of 1 to 10 μg/ml was measured. As a result, as shown in FIG. 42, the novel ginsenoside GS #10 of an embodiment of the present disclosure was shown to increase NO production in a concentration-dependent manner.

Thereafter, the NO production-increasing effect of the novel ginsenoside GS #10 was compared with other ginsenosides GS #01-GS #06 isolated from the conventional *Ginseng* seed extract, which are comparative examples of the present disclosure.

Figure 43:
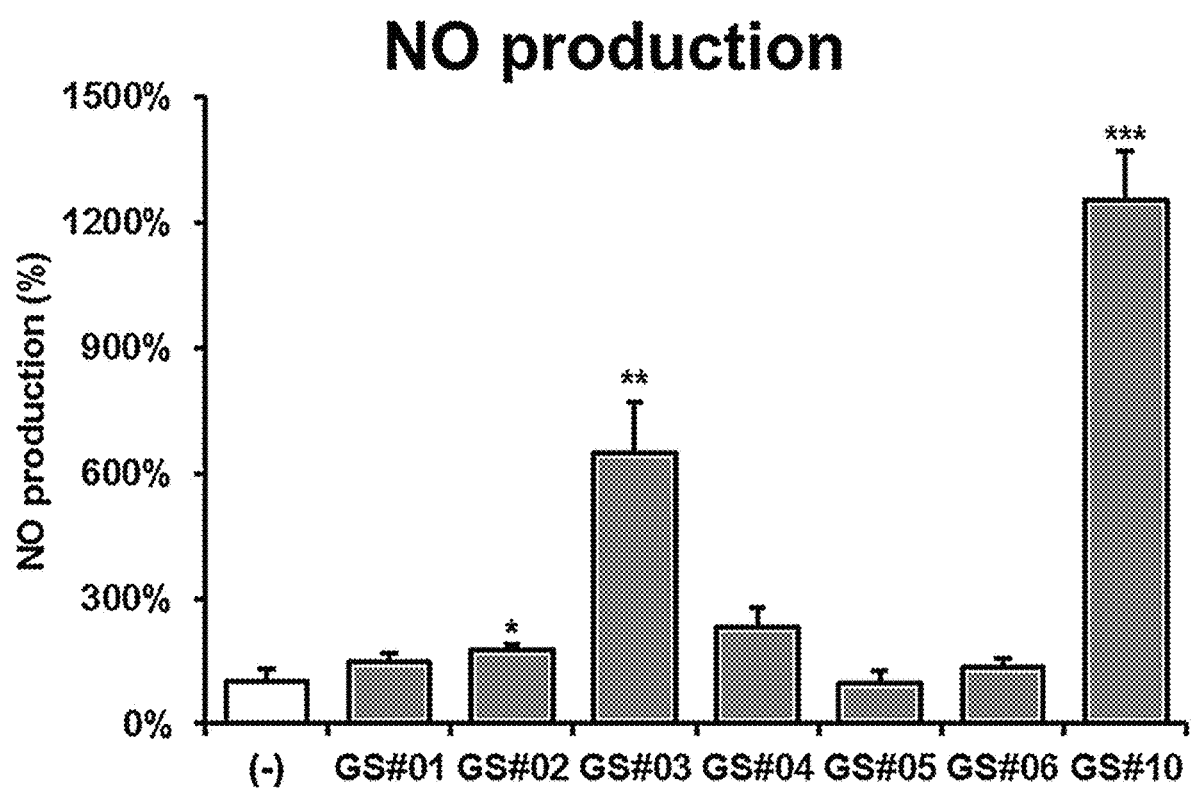
FIG. 43 is a diagram showing a comparison of the production amount of nitric oxide (NO) of GS #10 corresponding to the novel ginsenoside of the present disclosure isolated from *Ginseng* seed extract and the ginsenosides GS #01-GS #06, which are comparative examples of the present disclosure, at the same concentration. (* P<0.001 vs. (-),  P<0.01 vs. (-), * P<0.05 vs. (-))

As a result of treatment of ginsenosides GS #01 to GS #06 as comparative examples at a concentration of 10 μg/ml in human umbilical vascular endothelial cells in the same manner as above, as shown in FIG. 43, the novel ginsenoside GS #10 of an embodiment of the present disclosure was shown to have a significantly greater NO production-increasing effect than the conventional ginsenosides GS #01 to GS #06. In particular, it showed about 2 times or more better efficacy than ginsenoside Re (GS #03), which is known to have excellent NO production ability. This is due to the chemical structural difference, which means that the novel ginsenoside PG-RT$_8$ of the present disclosure is excellent in blood circulation improving effect among the *Ginseng* seed-derived ginsenosides.

[Test Example 13] Comparison of Vascular Anti-Aging Effect

If blood vessel aging is prevented or delayed by increasing the survival rate of vascular endothelial cells, blood circulation may be improved since blood vessel function may be maintained and loss of blood vessel elasticity may be prevented or improved.

Figure 44:
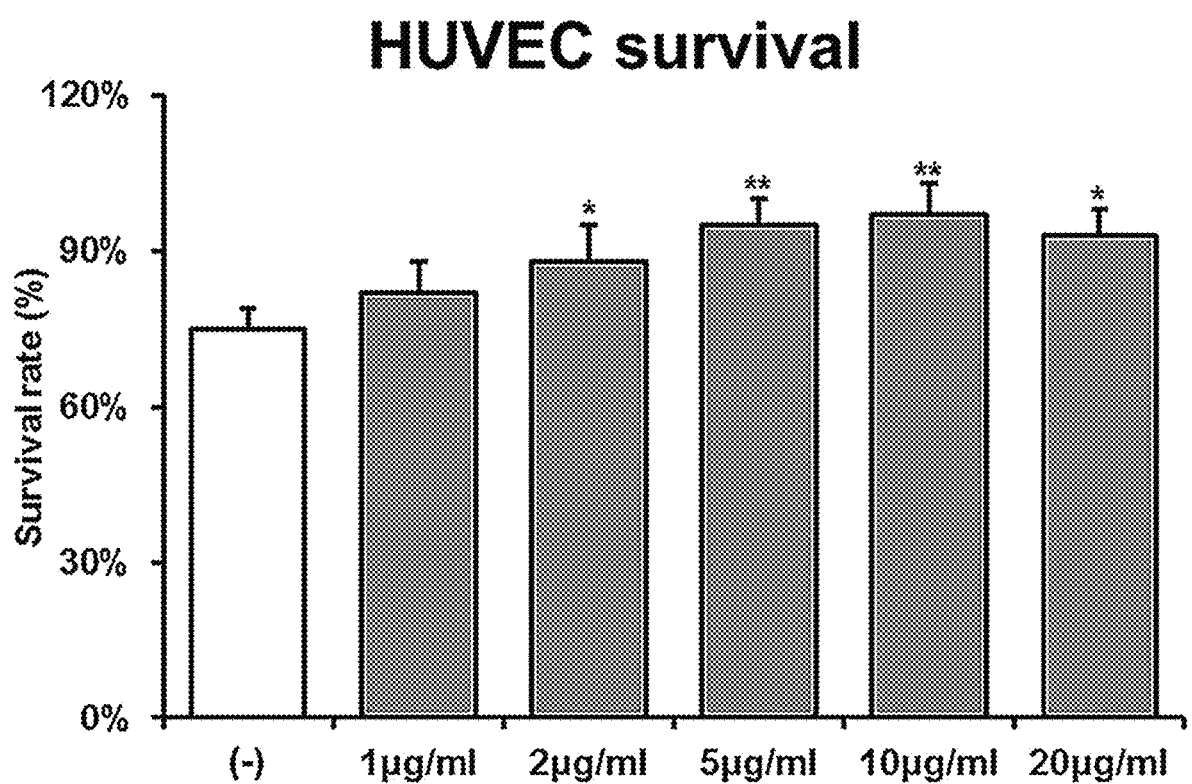
FIG. 44 is a diagram showing a measurement of the survival rate of human unbilical vein endothelial cells (HUVEC) according to the concentration of GS #10 corresponding to the novel ginsenoside of the present disclosure isolated from *Ginseng* seed extract. (*** P<0.001 vs. (-), * P<0.05 vs. (-))

In this experiment, it was confirmed whether the novel ginsenoside GS #10 of an embodiment of the present disclosure can increase the survival rate of vascular endothelial cells. Specifically, human umbilical vein endothelial cells (HUVECs) were purchased from the International Center for Biological Resources (ATCC) and cultured, and then the novel ginsenoside GS #10 was treated at a concentration of 1-10 μg/ml and MTT(3-(4,5-dimethylthiazol-2-yl)-2,5-diphenyltetrazolium bromide) analysis was performed to observe cell death. As a result, as shown in FIG. 44, the novel ginsenoside GS #10 of an embodiment of the present disclosure was shown to increase the survival rate of HUVEC regardless of the concentration.

Thereafter, the effect of increasing the survival rate of the vascular endothelial cells of the novel ginsenoside GS #10 was compared with other ginsenosides GS #01-GS #06 isolated from the conventional *Ginseng* seed extract, which are comparative examples of the present disclosure.

Figure 45:
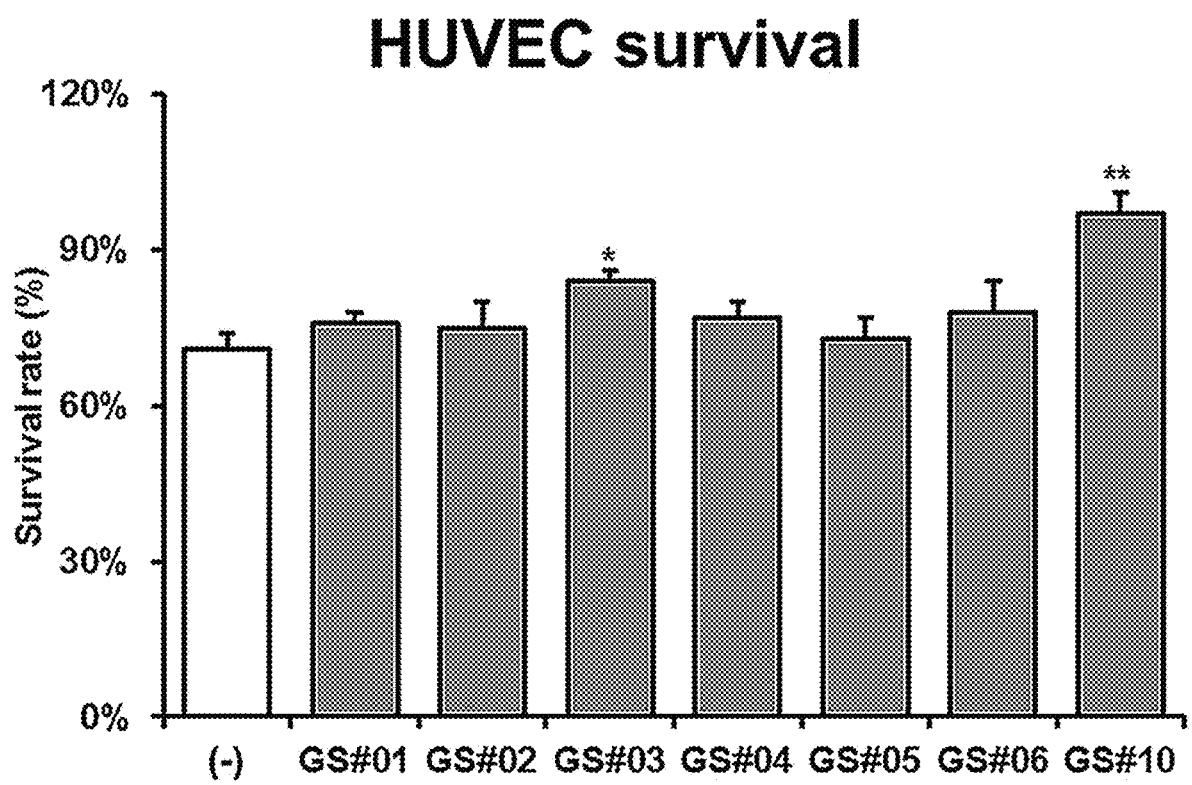
FIG. 45 is a diagram showing a comparison of the survival rate of human unbilical vein endothelial cells (HUVEC) of GS #10 corresponding to the novel ginsenoside of the present disclosure isolated from *Ginseng* seed extract and the ginsenosides GS #01-GS #06, which are comparative examples of the present disclosure, at the same concentration. (* P<0.001 vs. (−),  P<0.01 vs. (−), * P<0.05 vs. (−))

As a result of treatment of ginsenosides GS #01-GS #06, which are comparative examples at a concentration of 10 μg/ml to human vascular endothelial cells and MTT analysis, in the same manner as above, as shown in FIG. 45, the novel ginsenoside GS #10 of an embodiment of the present disclosure was found to have the highest survival rate-increasing effect of vascular endothelial cells.

[Test Example 14] Comparison of Blood Circulation Improving Effect

The blood flow-increasing and vascular anti-aging efficacy of the novel ginsenoside GS #10 of an embodiment of the present disclosure was compared with the ginsenosides Rg1, Rg3, and Rb1 (purchased from Sigma), which are red *Ginseng* index components, as comparative examples of the present disclosure.

The experiments were performed in the same manner as in Test Examples 12 and 13, wherein each ginsenoside was treated at a concentration of 10 µg/ml, respectively.

Figure 46:
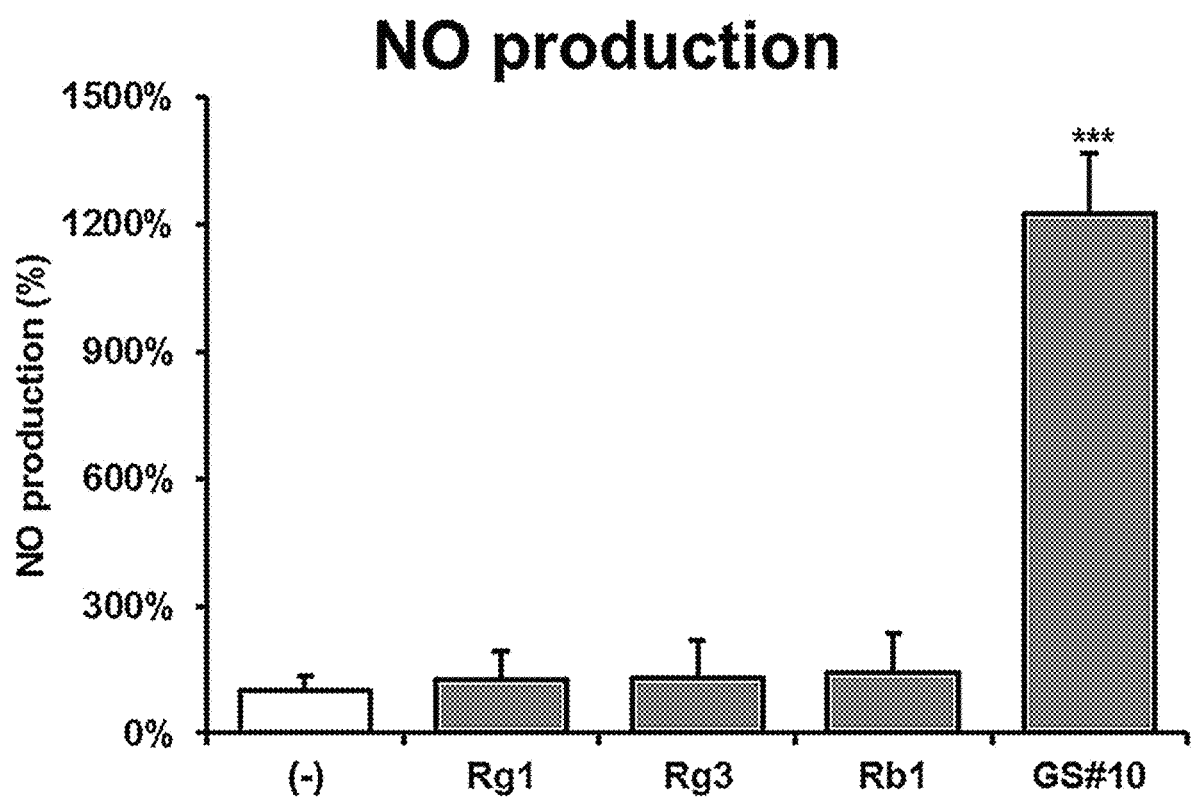
FIG. 46 is a diagram showing a comparison of the production amount of nitric oxide (NO) of ginsenosides Rg1, Rg3 and Rb1 of the red *Ginseng* index component and GS #10 corresponding to the novel ginsenoside of the present disclosure at the same concentration. (*** P<0.001 vs. (−), * P<0.05 vs. (−))
Figure 47:
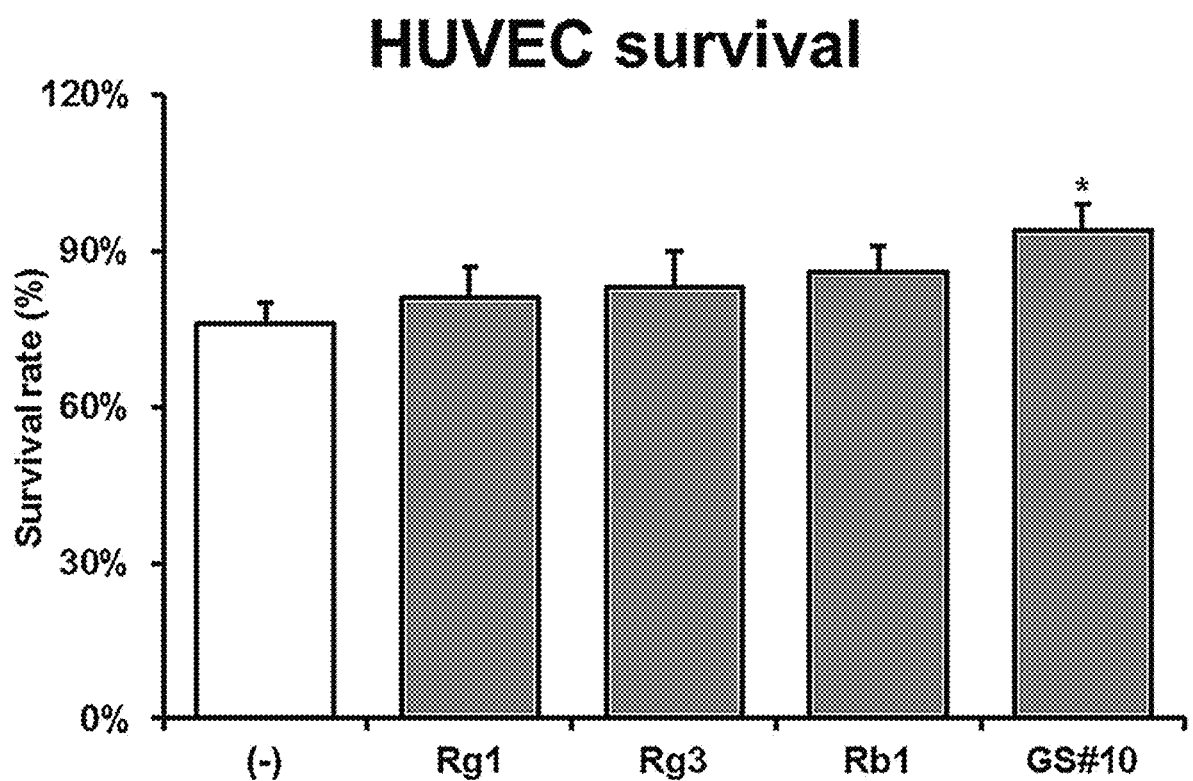
FIG. 47 is a diagram showing a comparison of the survival rate of human unbilical vein endothelial cells (HU-VEC) of ginsenosides Rg1, Rg3 and Rb1 of the red *Ginseng* index component and GS #10 corresponding to the novel ginsenoside of the present disclosure at the same concentration. (*** P<0.001 vs. (−), * P<0.05 vs. (−))

As a result, as shown in FIGS. 46 and 47, vascular anti-aging prevention effect of the novel ginsenoside GS #10 of the present disclosure through increased blood flow by increasing production of nitric oxide (NO) and increased survival rate of vascular endothelial cells (HUVEC) is far superior to ginsenosides Rg1, Rg3 and Rb1, which are red *Ginseng* index components.

Hereinafter, formulation examples of the composition according to one embodiment of the present specification will be explained. However, the formulation examples can be applied to various other formulations and are not intended to limit the present specification but only to specifically explain the present disclosure.

[Formulation Example 1] Softening Tonic (Skin Lotion)

The softening tonic was prepared in a conventional method according to the composition shown in the table below.

TABLE 3

| Compounding components | Contents (wt %) |
|---|---|
| PG-RT$_8$ | 0.1 |
| Glycerin | 3.0 |
| Butylene glycol | 2.0 |
| Propylene glycol | 2.0 |
| Carboxy vinyl polymer | 0.1 |
| PEG-12 nonylphenyl ether | 0.2 |
| Polysorbate 80 | 0.4 |
| Ethanol | 10.0 |
| Triethanolamine | 0.1 |
| Preservative, pigment, perfume | Proper amount |
| Purified water | Balance |

[Formulation Example 2] Nourishing Tonic (Milk Lotion)

The nourishing tonic was prepared in a conventional method according to the composition shown in the table below.

TABLE 4

| Compounding components | Contents (wt %) |
|---|---|
| PG-RT$_8$ | 0.1 |
| Glycerin | 3.0 |
| Butylene glycol | 3.0 |
| Propylene glycol | 3.0 |
| Carboxy vinyl polymer | 0.1 |
| Bees wax | 4.0 |
| Polysorbate 60 | 1.5 |
| Caprylic/Capric triglycerides | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Preservative, pigment, perfume | Proper amount |
| Purified water | Balance |

[Formulation Example 3] Massage Cream

The massage cream was prepared in a conventional method according to the composition shown in the table below.

TABLE 5

| Compounding components | Contents (wt %) |
|---|---|
| PG-RT$_8$ | 0.1 |
| Glycerin | 8.0 |
| Butylene glycol | 4.0 |
| Liquid paraffin | 45.0 |
| β-glucan | 7.0 |
| Carbomer | 0.1 |
| Caprylic/Capric triglycerides | 3.0 |
| Bees wax | 4.0 |
| Cetearyl glucoside | 1.5 |
| Sorbitan Sesquioleate | 0.9 |
| Vaseline | 3.0 |
| Paraffin | 1.5 |
| Preservative, pigment, perfume | Proper amount |
| Purified water | Balance |

[Formulation Example 4] Tablet 100 mg of ginsenoside PG-RT$_8$, 400 mg of lactose, 400 mg of corn starch, and 2 mg of magnesium stearate were mixed, and then tableted to prepare a tablet in accordance with a conventional method for preparing tablets.

[Formulation Example 5] Capsule 100 mg of ginsenoside PG-RT$_8$, 400 mg of lactose, 400 mg of corn starch, and 2 mg of magnesium stearate were mixed, and then filled into gelatin capsules to prepare a capsule in accordance with a conventional method for preparing capsules.

[Formulation Example 6] Granule 50 mg of ginsenoside PG-RT$_8$, 250 mg of anhydrous glucose and 550 mg of starch were mixed, molded into granules using a fluidized bed granulator, and then filled into a pouch.

[Formulation Example 7] Drink 50 mg of ginsenoside PG-RT$_8$, 10 g of glucose, 0.6 g of citric acid, and 25 g of liquid oligosaccharides were mixed, added with 300 ml of purified water, and 200 ml of the mixture was filled in a bottle. After the bottle was filled, the content was sterilized at 130° C. for 4-5 seconds to prepare a drink.

[Formulation Example 8] Caramel Formulation 50 mg of ginsenoside PG-RT$_8$, 1.8 g of corn syrup, 0.5 g of skim milk, 0.5 g of soy lecithin, 0.6 g of butter, 0.4 g of vegetable hardened oil, 1.4 g of sugar, 0.58 g of margarine, and 20 mg of table salt were mixed to prepare caramel.

[Formulation Example 9] Health Food

TABLE 6

| Components | Contents |
|---|---|
| PG-RT$_8$ | 100 mg |
| Vitamin mixture | |
| Vitamin A acetate | 70 µg |
| Vitamin E | 1.0 mg |
| Vitamin B1 | 0.13 mg |

TABLE 6-continued

| Components | Contents |
| --- | --- |
| Vitamin B2 | 0.15 mg |
| Vitamin B6 | 0.5 mg |
| Vitamin B12 | 0.2 µg |
| Vitamin C | 10 mg |
| Biotin | 10 µg |
| Nicotinic acid amide | 1.7 mg |
| Folic acid | 50 µg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

Although the composition ratio of the vitamin and inorganic mixture was obtained by a mixed composition using the components that are relatively suitable for health foods, it is irrelevant to arbitrarily modify the compounding ratio for carrying out the present disclosure. The above ingredients may be mixed according to the conventional method for preparing health foods, and then may be used for preparing a granule and preparing a health food composition according to the conventional method.

[Formulation Example 10] Healthy Drink

TABLE 7

| Components | Contents |
| --- | --- |
| PG-RT$_8$ | 10 mg |
| Citric acid | 1000 mg |
| Oligosaccharide | 100 g |
| Plum concentrate | 2 g |
| Taurine | 1 g |
| Purified water | Balance |
| Total volume | 900 Ml |

As shown in the table above, a balance of purified water was added to make a total volume of 900 ml, and the above components were mixed according to the conventional method for preparing a healthy drink, stirred and heated at 85° C. for about 1 hour, and then the resulting solution was filtered, obtained in a sterilized 2-liter container, sterilized sealed, and then refrigerated to prepare a healthy beverage composition.

[Formulation Example 11] Injection

Injections were prepared by conventional methods according to the compositions described in the table below.

TABLE 8

| Compounding components | Contents (wt %) |
| --- | --- |
| PG-RT$_8$ | 10-50 mg |
| Sterile distilled water for injection | Proper amount |
| pH regulator | Proper amount |

The present disclosure may provide the following embodiments as an example.

In a first embodiment, there may be provided a method for one or more of metabolic control and blood circulation improvement comprising administering to a subject in need thereof an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

In a second embodiment, in accordance with the first embodiment, there may be provided a method, wherein the (20S,24R)-6-O-β-D-glucopyranosyl(1→2)-β-D-glucopyranoside-dammar-3-one-20,24-epoxy-6a,12b,25-triol has the structure of following formula 1.

[Formula 1]

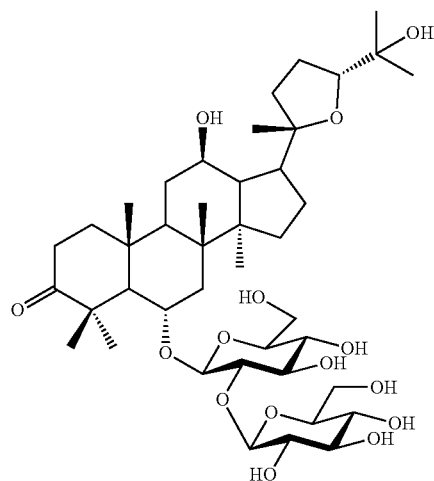

In a third embodiment, in accordance with the first or second embodiment, there may be provided a method, wherein the (20S,24R)-6-O-β-D-glucopyranosyl(1→2)-β-D-glucopyranoside-dammar-3-one-20,24-epoxy-6a,12b,25-triol is extracted from *Ginseng* seed.

In a fourth embodiment, in accordance with any one or more of the first to third embodiments, there may be provided a method, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof lowers blood sugar.

In a fifth embodiment, in accordance with any one or more of the first to fourth embodiments, there may be provided a method, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof inhibits glycolysis in the blood.

In a sixth embodiment, in accordance with any one or more of the first to fifth embodiments, there may be provided a method, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof promotes cellular uptake of glucose in the blood.

In a seventh embodiment, in accordance with any one or more of the first to sixth embodiments, there may be provided a method, wherein the method comprises preventing or treating diabetes or diabetic complications.

In an eighth embodiment, in accordance with any one or more of the first to seventh embodiments, there may be provided a method, wherein the metabolic control comprises one or more of blood sugar control, lipid metabolism control or inhibition, cholesterol control, and anti-obesity.

In a ninth embodiment, in accordance with any one or more of the first to eighth embodiments, there may be provided a method, wherein the method comprises preventing or improving one or more selected from the group consisting of hypertension, diabetes, hyperlipidemia, hypertriglyceridemia, myocardial infarction, angina pectoris, arteriosclerosis, and hypercholesterolemia.

In a tenth embodiment, in accordance with any one or more of the first to ninth embodiments, there may be provided a method, wherein method comprises inhibiting adipocyte differentiation.

In an eleventh embodiment, in accordance with any one or more of the first to tenth embodiments, there may be provided a method, wherein the method comprises inhibiting lipid synthesis or accumulation in the body.

In a twelfth embodiment, in accordance with any one or more of the first to eleventh embodiments, there may be provided a method, wherein the method comprises increasing blood flow.

In a thirteenth embodiment, in accordance with any one or more of the first to twelfth embodiments, there may be provided a method, wherein the method comprises improving skin tone.

In a fourteenth embodiment, in accordance with any one or more of the first to thirteenth embodiments, there may be provided a method, wherein the dosage of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof is 0.05 mg/kg/day to 10 g/kg/day.

In a fifteenth embodiment, in accordance with any one or more of the first to fourteenth embodiments, there may be provided a method, wherein the method comprises administering to a subject of one or more of a subject with reduced glycemic control capacity, a subject with reduced lipid metabolic control capacity, a subject with reduced cholesterol metabolic control capacity, an obese subject and a subject with poor blood circulation.

In a sixteenth embodiment, in accordance with any one or more of the first to fifteenth embodiments, there may be provided a method, wherein the method comprises a transdermal administration of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

In a seventeenth embodiment, in accordance with any one or more of the first to sixteenth embodiments, there may be provided a method, wherein the method comprises an oral or parenteral administration of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

The above embodiments have been disclosed for the purposes of illustration, and the description is not intended to limit the scope of the present disclosure. Accordingly, various modifications, variations, and substitutions may occur to those skilled in the art without departing from the spirit and scope of the present disclosure.

What is claimed is:

1. A method for one or more of metabolic control and blood circulation improvement comprising administering to a subject in need thereof an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

2. The method of claim 1, wherein the (20S,24R)-6-O-β-D-glucopyranosyl(1→2)-β-D-glucopyranoside-dammar-3-one-20,24-epoxy-6a,12b,25-triol has the structure of following formula 1:

[Formula 1]

3. The method of claim 1, wherein the (20S,24R)-6-O-β-D-glucopyranosyl(1→2)-β-D-glucopyranoside-dammar-3-one-20,24-epoxy-6a,12b,25-triol is extracted from *Ginseng* seed.

4. The method of claim 1, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof lowers blood sugar.

5. The method of claim 1, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof inhibits glycolysis in the blood.

6. The method of claim 1, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof promotes cellular uptake of glucose in the blood.

7. The method of claim 1, wherein the method comprises preventing or improving diabetes or diabetic complications.

8. The method of claim 1, wherein the metabolic control comprises one or more of blood sugar control, lipid metabolism control or inhibition, cholesterol control, and anti-obesity.

9. The method of claim 1, wherein the method comprises preventing or improving one or more selected from the group consisting of hypertension, diabetes, hyperlipidemia, hypertriglyceridemia, myocardial infarction, angina pectoris, arteriosclerosis, and hypercholesterolemia.

10. The method of claim 1, wherein method comprises inhibiting adipocyte differentiation.

11. The method of claim 1, wherein the method comprises inhibiting lipid synthesis or accumulation in the body.

12. The method of claim 1, wherein the method comprises increasing blood flow.

13. The method of claim 1, wherein the method comprises improving skin tone.

14. The method of claim 1, wherein the dosage of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof is 0.5 mg/kg/day to 10 g/kg/day.

15. The method of claim 1, wherein the method comprises administering to a subject with one or more of reduced glycemic control capacity reduced lipid metabolic control capacity, reduced cholesterol metabolic control capacity, obesity and poor blood circulation.

16. The method of claim 1, wherein the method comprises transdermal administration of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

17. The method of claim 1, wherein the method comprises oral or parenteral administration of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

* * * * *